(12) United States Patent
Ishida

(10) Patent No.: US 11,819,674 B2
(45) Date of Patent: Nov. 21, 2023

(54) CATHETER ASSEMBLY

(71) Applicant: TERUMO KABUSHIKI KAISHA, Tokyo (JP)

(72) Inventor: Masahiro Ishida, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 133 days.

(21) Appl. No.: 17/571,141

(22) Filed: Jan. 7, 2022

(65) Prior Publication Data
US 2022/0126026 A1 Apr. 28, 2022

Related U.S. Application Data

(63) Continuation of application No. 16/906,157, filed on Jun. 19, 2020, now Pat. No. 11,253,656, which is a (Continued)

(30) Foreign Application Priority Data

Dec. 20, 2017 (JP) .................................. 2017-243604

(51) Int. Cl.
*A61M 5/32* (2006.01)
*A61M 25/00* (2006.01)
(Continued)

(52) U.S. Cl.
CPC ............ *A61M 5/3286* (2013.01); *A61M 1/16* (2013.01); *A61M 5/158* (2013.01);
(Continued)

(58) Field of Classification Search
CPC .............. A61M 25/008; A61M 25/005; A61M 25/0606; A61M 5/3293; A61M 1/36;
(Continued)

(56) References Cited

U.S. PATENT DOCUMENTS

2004/0015138 A1 1/2004 Currier et al.
2011/0282285 A1 11/2011 Blanchard et al.
(Continued)

FOREIGN PATENT DOCUMENTS

CN 1671429 A 9/2005
CN 201006151 Y 1/2008
(Continued)

OTHER PUBLICATIONS

Second Chinese Office Action on CN Appl. Ser. No. 201880079667.1 dated Feb. 21, 2022 (10 pages).
(Continued)

*Primary Examiner* — Phillip A Gray
(74) *Attorney, Agent, or Firm* — Foley & Lardner LLP

(57) ABSTRACT

A catheter assembly includes: a catheter including a circumferential wall and a distal opening; an inner needle inserted through the catheter, the inner needle having a sharp needle tip at a distal end of the inner needle; and a deflection suppression mechanism that supports the inner needle via the catheter to suppress deflection of the inner needle, the deflection suppression mechanism including a contact support portion that is configured to support the catheter when the catheter is advanced with respect to the inner needle. The circumferential wall of the catheter includes one or more side holes. In an initial state before the catheter is advanced with respect to the inner needle, the contact support portion is located proximal of a distal-most one of the one or more side holes and a gap is formed between an outer surface of the catheter and an inner surface of the contact support portion.

20 Claims, 21 Drawing Sheets

Related U.S. Application Data continuation of application No. PCT/JP2018/046728, filed on Dec. 19, 2018.

(51) Int. Cl.
  *A61M 1/16* (2006.01)
  *A61M 5/158* (2006.01)
  *A61M 25/06* (2006.01)

(52) U.S. Cl.
  CPC ........ *A61M 5/3293* (2013.01); *A61M 25/005* (2013.01); *A61M 25/008* (2013.01); *A61M 25/065* (2013.01); *A61M 25/0606* (2013.01); *A61M 25/0693* (2013.01)

(58) Field of Classification Search
  CPC .. A61M 5/3286; A61M 5/158; A61M 25/065; A61M 25/06; A61M 1/16
  See application file for complete search history.

(56) References Cited

U.S. PATENT DOCUMENTS

| | | | |
|---|---|---|---|
| 2013/0053826 A1* | 2/2013 | Shevgoor | A61M 25/0015 604/523 |
| 2015/0051583 A1* | 2/2015 | Horvath | A61M 25/0015 604/508 |
| 2015/0051584 A1 | 2/2015 | Korkuch et al. | |
| 2016/0331939 A1* | 11/2016 | Ishida | A61M 25/0606 |
| 2017/0203033 A1 | 7/2017 | Horvath et al. | |

FOREIGN PATENT DOCUMENTS

| | | |
|---|---|---|
| CN | 101121055 A | 2/2008 |
| CN | 105102053 A | 11/2015 |
| CN | 206454070 U | 9/2017 |
| JP | 2009-142357 A | 7/2009 |
| JP | 5108882 B2 | 12/2012 |
| JP | 2015-503422 A | 2/2015 |
| JP | 2016-168085 A | 9/2016 |
| JP | 2016-530934 A | 10/2016 |
| WO | WO-99/29361 A1 | 6/1999 |
| WO | WO-2009/049823 A1 | 4/2009 |
| WO | WO-2015/115315 A1 | 8/2015 |
| WO | WO-2016/020923 A2 | 2/2016 |
| WO | WO-2016/185909 A1 | 11/2016 |
| WO | WO-2017/051801 A1 | 3/2017 |

OTHER PUBLICATIONS

International Searching Authority, "International Search Report," issued in connection with International Patent Application No. PCT/JP2018/046728, dated Feb. 5, 2019.

International Searching Authority, "Written Opinion," issued in connection with International Patent Application No. PCT/JP2018/046728, dated Feb. 5, 2019.

Extended European Search Report dated Nov. 27, 2020 in European Patent Application No. 18890114.4.

Office Action dated Oct. 9, 2021 issued in a corresponding Chinese Patent Application No. 201880079667.1, (19 pages).

European Office Action issued in connection with EP Appl. Ser. No. 18890114.4 dated May 30, 2023.

Japanese Office Action issued in connection with JP Appl. Ser. No. 2022-123694 dated Jun. 6, 2023.

* cited by examiner

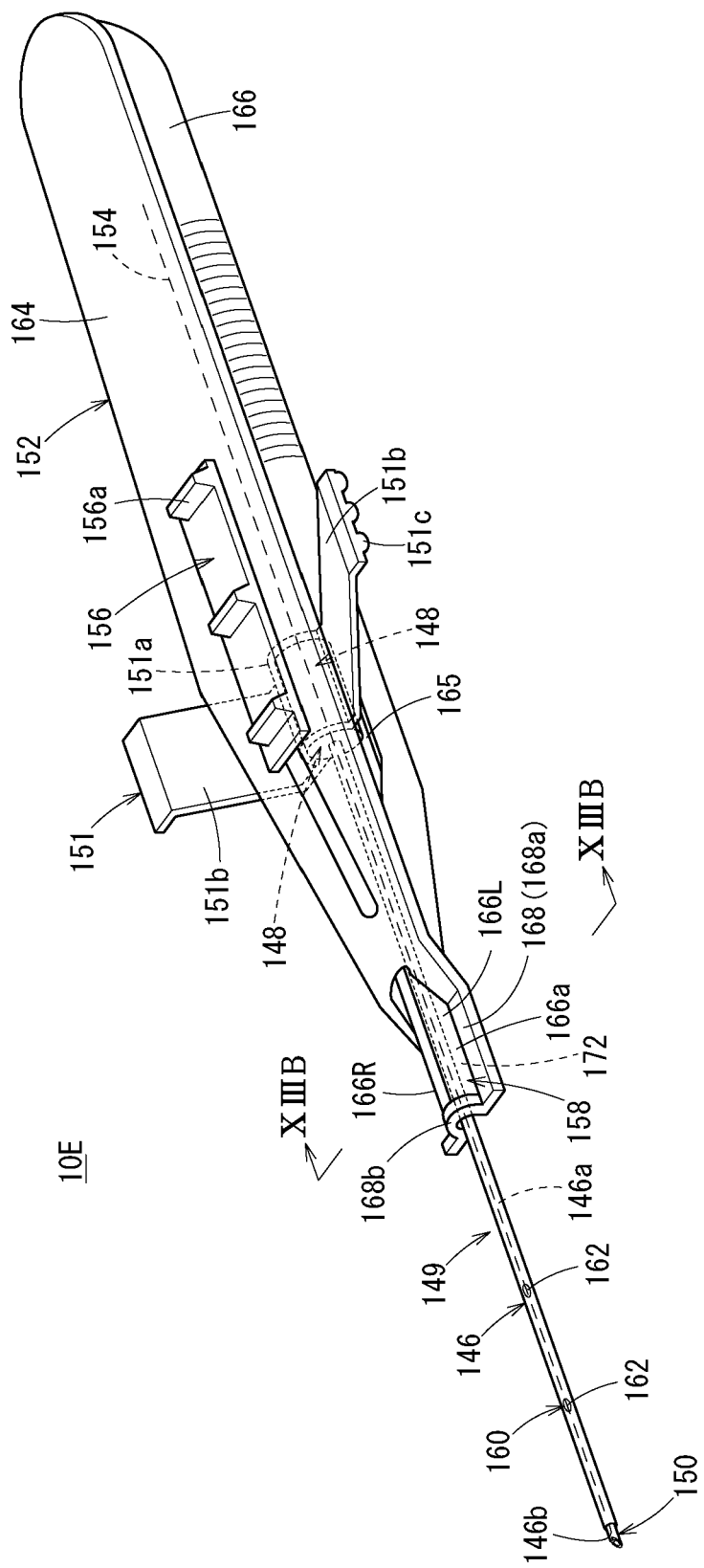

CATHETER ASSEMBLY

CROSS-REFERENCE TO RELATED APPLICATIONS

This is a Continuation of U.S. patent application Ser. No. 16/906,157, filed on Jun. 19, 2020, which is a Bypass Continuation of PCT Application No. PCT/JP2018/046728, filed on Dec. 19, 2018, which claims priority to Japanese Application No. 2017-243604, filed on Dec. 20, 2017. The contents of these applications are hereby incorporated by reference in their entireties.

BACKGROUND

The present disclosure relates to a catheter assembly that punctures a blood vessel and causes a catheter to indwell, for example, in order to perform an infusion or hemodialysis to a patient.

Conventionally, for example, a catheter assembly has been used in order to perform an infusion, hemodialysis, or the like to a patient. This kind of catheter assembly includes a catheter, a catheter hub fixed to a proximal end of the catheter, an inner needle that is inserted into the catheter, and a needle hub fixed to a proximal end of the inner needle (for example, JP 5108882 B2). In use of the catheter assembly, a blood vessel of a patient is punctured with the catheter together with the inner needle, and the inner needle is withdrawn from the catheter after this puncture in the state of puncturing the patient with the catheter. Accordingly, the catheter is indwelled in the patient's blood vessel.

SUMMARY

In the case of using a catheter assembly for an infusion or hemodialysis, it is difficult to suction blood if a catheter distal end is pasted to a blood vessel wall or the catheter distal end is crushed during blood suction. In addition, an inner needle easily deflects, for example, in the case of puncturing a patient with a catheter assembly having a relatively long catheter for the purpose of an intravenous infusion. If the inner needle deflects at the time of puncture, it is difficult to perform the puncture.

Certain embodiments of the present invention have been developed in view of such problems, and an object thereof is to provide a catheter assembly capable of blood suction without hindrance and suppressing a deflection of a needle at the time of puncture.

In order to achieve the above object, provided are: a catheter having a distal opening; an inner needle inserted into the catheter; and a deflection suppression mechanism that supports the inner needle via the catheter to suppress a deflection of the inner needle. The catheter is provided with a side flow path structure, which has at least one liquid passage that allows passage of a liquid between an inside and an outside of the catheter, on a circumferential wall. The deflection suppression mechanism has a sliding contact support portion that is capable of supporting the catheter while sliding against the catheter when the catheter is advanced with respect to the inner needle. The sliding contact support portion is located to be closer to a proximal side than a liquid passage located on a most distal side of the side flow path structure in an initial state before the catheter is advanced with respect to the inner needle.

According to certain embodiments of the catheter assembly configured as described above, the deflection suppression mechanism that supports the inner needle via the catheter to suppress the deflection of the inner needle is provided, and thus, the deflection of the inner needle at the time of puncture is suppressed. Accordingly, the stable puncture is possible. Because the liquid passage is provided on the circumferential wall of the catheter, blood can be suitably suctioned in the case of using the catheter for an infusion or hemodialysis. Because the sliding contact support portion is located to be closer to the proximal side than the liquid passage in the initial state, damage of the liquid passage can be suppressed, and a variation in sliding resistance at the time of advancing the catheter can be suppressed.

The sliding contact support portion may be provided to be closer to the proximal side than a liquid passage located on the most proximal side in the side flow path structure.

With this configuration, it is possible to prevent damage of all of the liquid passages, and to suppress the variation in sliding resistance with respect to the deflection suppression mechanism at the time of advancing the catheter as much as possible.

The sliding contact support portion may be provided to be slightly closer to the proximal side than the liquid passage located on the most proximal side.

With this configuration, the catheter can be effectively supported by the deflection suppression mechanism within a range that does not interfere with the liquid passage.

The side flow path structure may include a plurality of liquid passages arranged at intervals along a longitudinal direction of the catheter.

With this configuration, the number of liquid passages is large, and thus, blood can be reliably suctioned regardless of how the catheter is brought into contact with the blood vessel. Because the number of the liquid passages is large, the total opening area of the liquid passages can be increased, and a suction resistance can be reduced, and thus, blood can be easily suctioned. Further, a size of each of the liquid passages can be reduced, and thus, a resistance when the liquid passage passes through a blood vessel wall decreases, and an operation of inserting the catheter into the blood vessel is further facilitated.

The liquid passage located on the most proximal side may be provided in a lower portion of the catheter.

With this configuration, when the catheter indwelling in a blood vessel comes out of the blood vessel, the liquid passage hardly comes out of the blood vessel because the liquid passage provided on the most proximal side faces downward. That is, when the catheter comes out of the blood vessel, the liquid passage on the most proximal side that faces downward is caught on the blood vessel wall. Then, the other liquid passage is located in the blood vessel.

The side flow path structure may include only one liquid passage provided at a circumferential position corresponding to a circumferential position of a portion of the catheter that contacts the sliding contact support portion.

With this configuration, the liquid passage does not slide with respect to the sliding contact support portion even if a large liquid passage is provided to facilitate suction, and thus, the liquid passage is not damaged. In addition, the puncture is easy because there is only one-time resistance when the liquid passage passes through the blood vessel wall.

The catheter may include: a catheter body and a flexible portion that is provided at a distal portion of the catheter body, includes a most distal portion of the catheter, and is more flexible than the catheter body.

With this configuration, it is possible to suppress the distal end of the catheter from being caught on a back wall of the blood vessel even when a puncture angle is large. Accordingly, it is possible to prevent the catheter from being hardly inserted into a blood vessel or to prevent a blood vessel wall from being damaged by the catheter distal end.

The deflection suppression mechanism may have a lower support member that supports the catheter from a lower side, the lower support member may have the sliding contact support portion, and the side flow path structure may be provided only in a lower portion of the catheter.

The catheter may have a tapered portion whose outer diameter decreases toward a distal side, the lower support member may be capable of elastically supporting the catheter, the side flow path structure may be provided in the tapered portion, and the sliding contact support portion may be located to be closer to the proximal side than the tapered portion in the initial state before the catheter is advanced with respect to the inner needle.

In this configuration, the tapered portion contacts the lower support member due to a spring property of the lower support member, but a beneficial effect is exhibited because the liquid passage structure is provided to be closer to the distal side than the sliding contact support portion.

The liquid passage may be a side hole provided with a flap protruding toward an inner side of an opening.

With this configuration, an opening area is increased by the movement of the flap during blood suction, so that blood can be efficiently suctioned. In addition, at least the flap on the most distal side does not slide with respect to a needle support at the time of advancing the catheter, so that damage of the flap can be suppressed.

The side flow path structure may be provided only in an upper portion of the catheter.

With this configuration, blood is easily suctioned because the liquid passage is in the upper portion even when the distal end of the catheter obliquely indwells.

The plurality of liquid passages may be open in different directions with respect to an axis of the catheter.

With this configuration, a medicinal solution is released in a plurality of directions in the blood vessel at the time of administering the medicinal solution, and reactions cancel each other out, so that the catheter hardly moves in the blood vessel. Therefore, it is possible to prevent the catheter from deviating from an appropriate indwelling position.

The plurality of liquid passages may be open in directions inclined with respect to the axis of the catheter.

In this configuration, an edge is formed by providing the liquid passage obliquely, but breakage of the edge is effectively prevented because the liquid passage does not slide with respect to the sliding contact support portion of the deflection suppression mechanism.

Rings each of which is made of a material harder than the catheter may be embedded in the catheter.

With this configuration, the catheter is reinforced by the ring, and thus, it is possible to prevent the catheter from being crushed in the blood vessel during blood suction.

The at least one liquid passage may be provided at any one or more locations of a distal side of the ring, the ring itself, a portion between the ring and the ring, a proximal side of the ring, a distal boundary of the ring, and a proximal boundary of the ring.

The catheter may include: a straight portion whose outer diameter is constant in an axial direction; and a tapered portion that is provided to be closer to the distal side than the straight portion and has an outer diameter that decreases toward the distal side, and the ring may be provided at any one or more locations of the tapered portion and the straight portion.

The liquid passage may have a form of a slit that is open depending on a pressure in a lumen of the catheter.

With this configuration, the slit is closed when no pressure is applied to the lumen of the catheter, and thus, the slit is closed at the time of inserting the catheter into a blood vessel. Therefore, it is possible to suppress the resistance when the side flow path structure passes through the blood vessel wall. On the other hand, the slit is open when a positive pressure and a negative pressure are applied to the lumen of the catheter, and thus, it is possible to administer the medicinal solution into the blood vessel or to suction the blood without any trouble.

The sliding contact support portion may include: an upper support portion capable of supporting the catheter from an upper side; and a transverse support portion capable of supporting the catheter from a transverse direction, and the slit may be provided only at any one location of an upper portion and a transverse portion of the catheter.

With this configuration, it is possible to effectively suppress damage of the slit and an increase in sliding resistance at the time of advancing the catheter.

According to certain embodiments of the catheter assembly, blood can be suctioned without any trouble, the deflection of the needle at the time of puncture can be suppressed.

BRIEF DESCRIPTION OF DRAWINGS

FIG. 12 is a perspective view of a catheter assembly according to a fifth embodiment of the present invention.

DETAILED DESCRIPTION

Hereinafter, embodiments of a catheter assembly according to the present invention will be described with reference to the accompanying drawings.

First Embodiment

Figure 1:
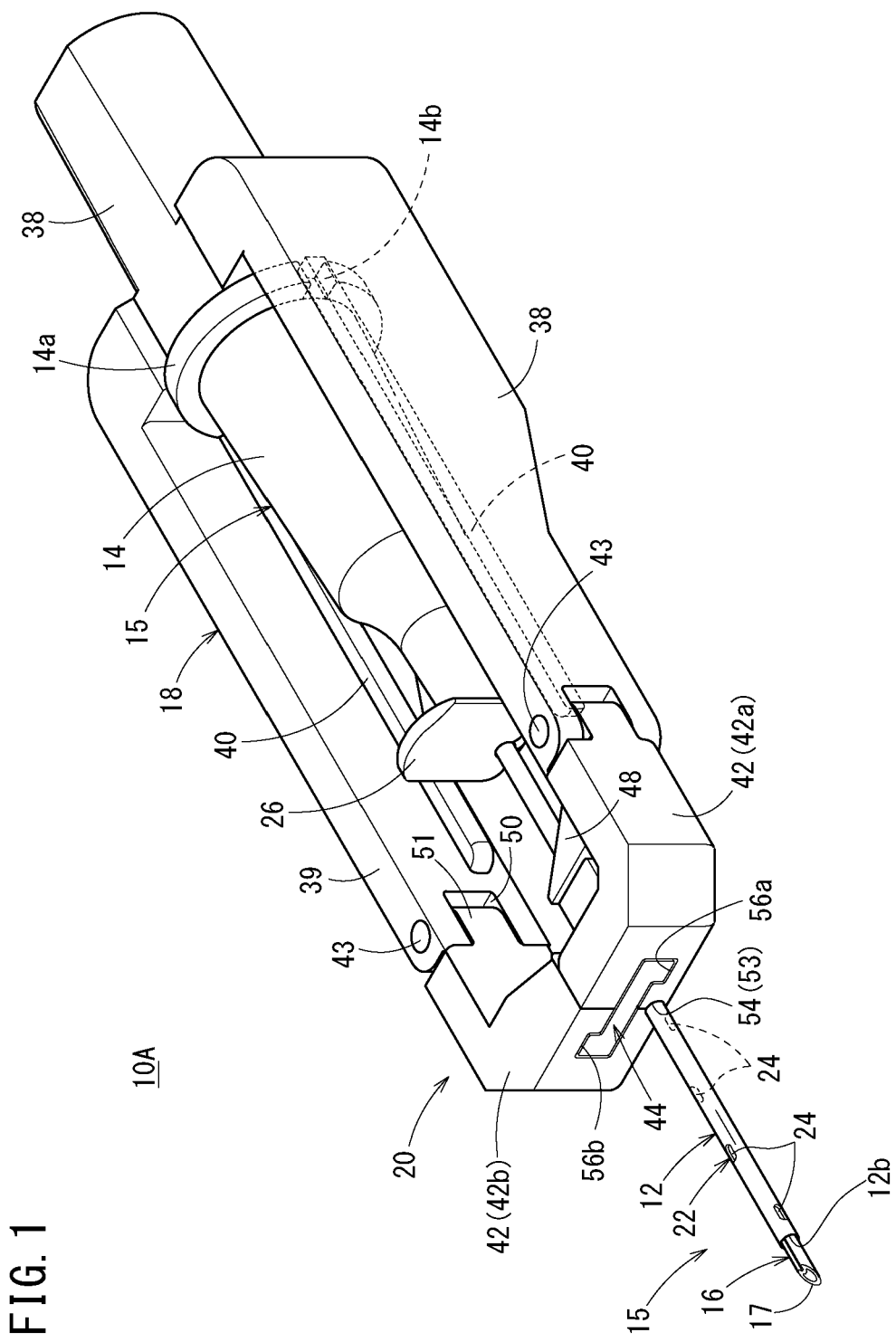
FIG. 1 is a perspective view of a catheter assembly according to a first embodiment of the present invention.
Figure 2:
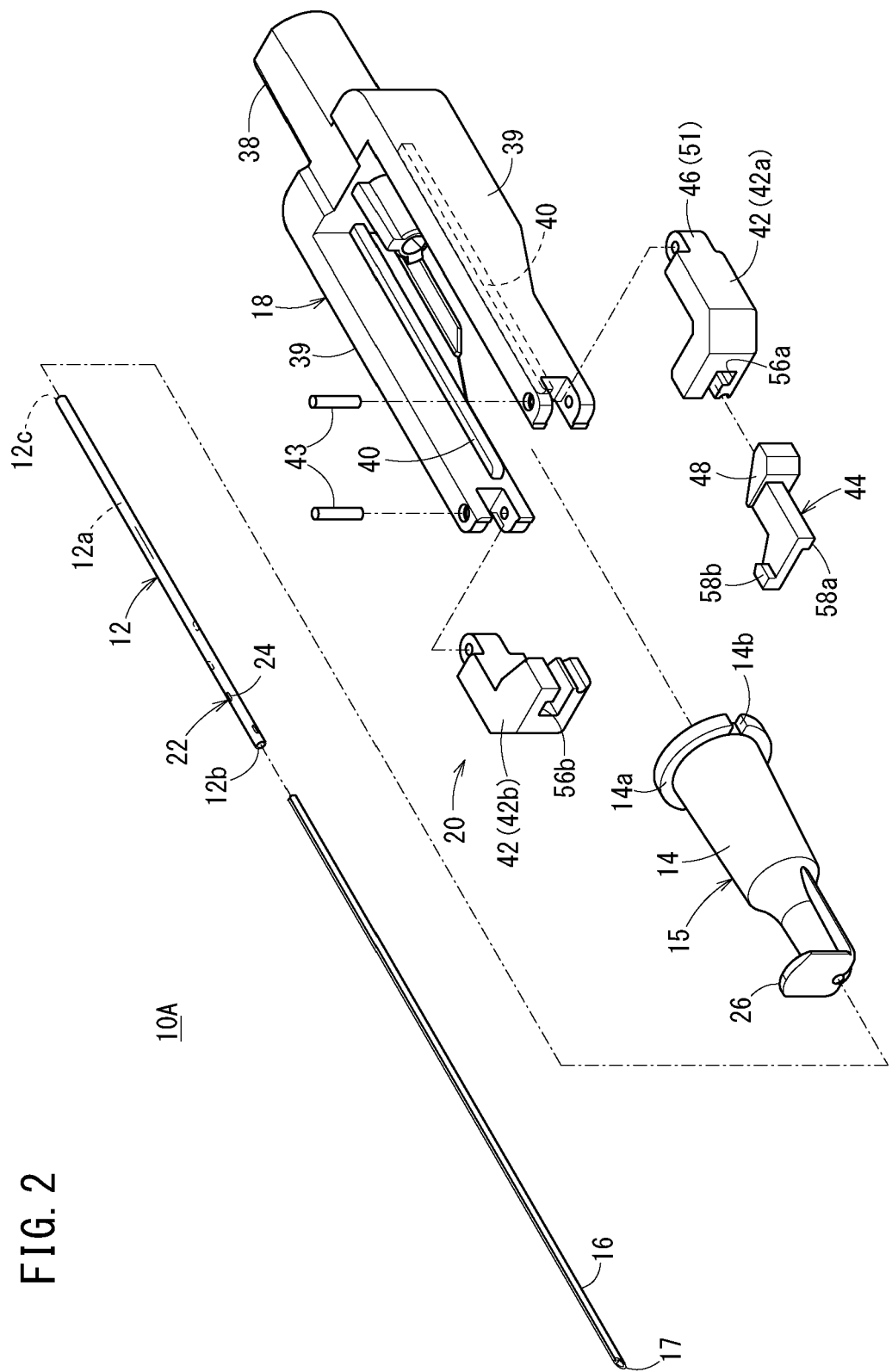
FIG. 2 is an exploded perspective view of the catheter assembly illustrated in FIG. 1.

As illustrated in FIGS. 1 and 2, a catheter assembly 10A according to a first embodiment includes: a catheter 12; a catheter hub 14 connected to a proximal side of the catheter 12; an inner needle 16 that has a sharp needle tip 17 at a distal end and is inserted through the catheter 12; a needle hub 18 connected to the inner needle 16; and a deflection suppression mechanism 20 that suppresses a deflection of the inner needle 16 at the time of puncture.

In the catheter assembly 10A, the needle hub 18 is gripped and operated by a user (a doctor, a nurse, or the like) to puncture a blood vessel of a patient with a distal portion thereof. In an initial state before use (before puncturing a patient), the catheter assembly 10A forms a double-tube structure in which the inner needle 16 is inserted through the catheter 12, and the inner needle 16 protrudes from a distal end of the catheter 12 by a predetermined length.

In the catheter assembly 10A in the initial state illustrated in FIG. 1, the double-tube structure of the catheter 12 and the inner needle 16, the catheter hub 14, the needle hub 18, and the deflection suppression mechanism 20 are combined to constitute one assembly and can be handled integrally.

The catheter 12 is a small-diameter tubular member that is flexible. The catheter 12 may be used as a catheter having a longer length than a peripheral venous catheter, for example, a central venous catheter, a peripheral inserted central catheter (PICC), a mid-line catheter, and the like. Incidentally, the catheter 12 may be used as the peripheral venous catheter. The catheter 12 is not limited to the venous catheter, and may be configured as an arterial catheter such as a peripheral arterial catheter. As a constituent material of the catheter 12, a resin material, particularly, a soft resin material is suitable.

As illustrated in FIG. 2, the catheter 12 has: a lumen 12a penetrating through the catheter 12 in the axial direction; a distal opening 12b open at the distal end of the catheter 12; and a proximal opening 12c open at a proximal end of the catheter 12.

Figure 3:
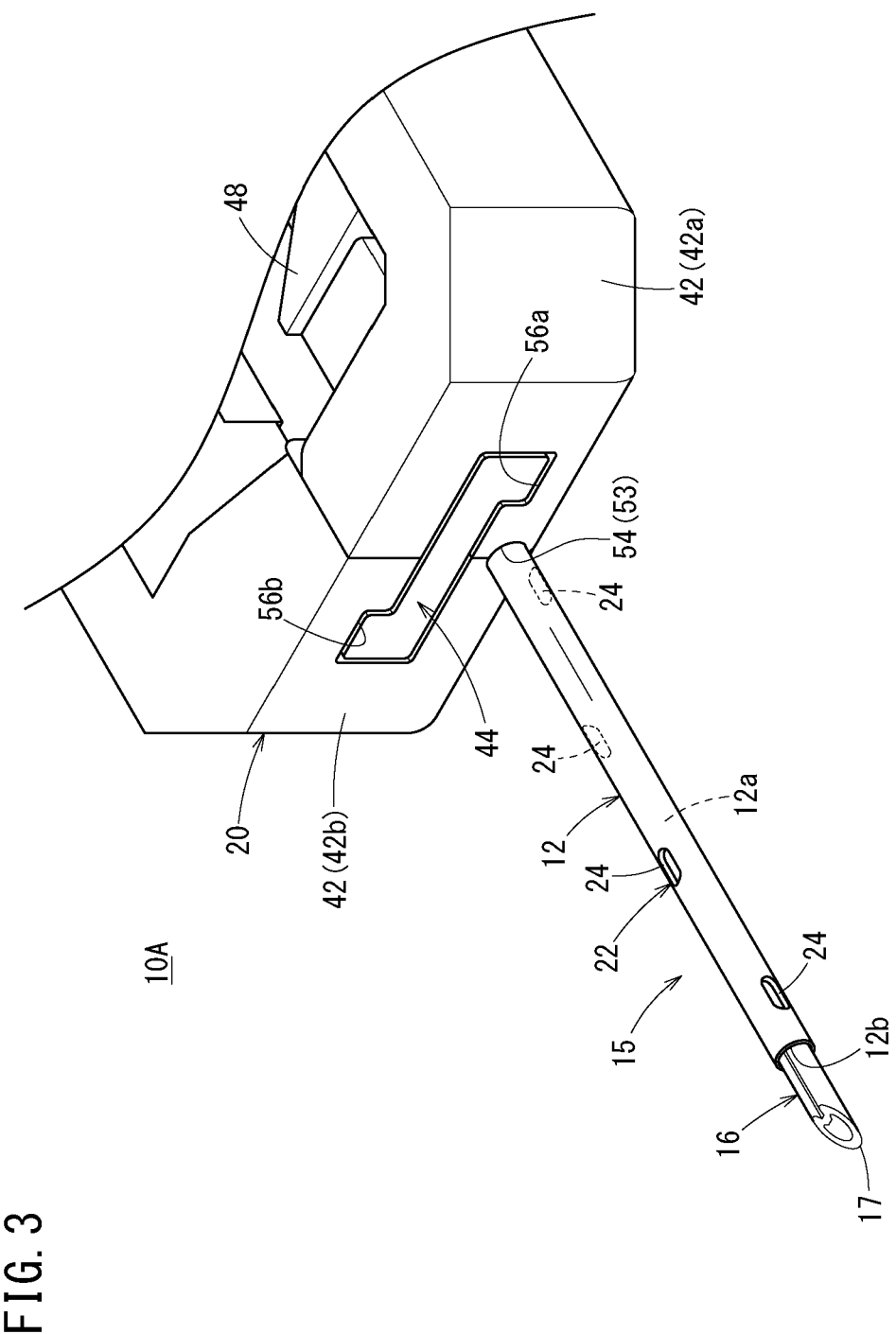
FIG. 3 is an enlarged view of a distal side of the catheter assembly illustrated in FIG. 1.

As illustrated in FIG. 3, a side flow path structure 22, which has at least one liquid passage that allows passage of a liquid between an inside and an outside of the catheter 12, is provided on a circumferential wall of the catheter 12. In the first embodiment, a side hole 24 penetrating from an inner circumferential surface to an outer circumferential surface of the circumferential wall of the catheter 12 is provided as the liquid passage. The side flow path structure 22 has a plurality of (four) side holes 24 provided at intervals in the longitudinal direction of the catheter 12. In the first embodiment, the side holes 24 are open in a left side surface, an upper surface, a right side surface, and a lower surface of the catheter 12 in order from the distal side to the proximal side. Therefore, the side hole 24 provided on the most proximal side is open downward. The plurality of side holes 24 may be formed in the same size, or may be formed in different sizes from each other.

As illustrated in FIG. 1, the catheter hub 14 is connected and fixed to the proximal end of the catheter 12. The catheter 12 and the catheter hub 14 constitute a catheter member 15. As illustrated in FIG. 2, a proximal end of the catheter hub 14 is provided with a flange portion 14a that protrudes outward and extends in the circumferential direction. Notches 14b are provided on both left and right sides of the flange portion 14a.

The catheter hub 14 is provided with a hub operation portion 26 configured to operate the catheter hub 14. The hub operation portion 26 in the illustrated example is a tab that protrudes upward from a distal end of the catheter hub 14, and is integrally molded with the catheter hub 14. The hub operation portion 26 may be configured as a separate component from the catheter hub 14 and may be detachable from the catheter hub 14. A user can operate the catheter hub 14 in the axial direction by touching and gripping or pressing the hub operation portion 26. The hub operation portion 26 may be configured to be detachable from the catheter hub 14.

At the time of use of the catheter assembly 10A, the catheter hub 14 is exposed on patient's skin in the state of puncturing a blood vessel with the catheter 12 and is pasted onto the skin with a dressing material, a tape, or the like to remain indwelled. Such a catheter hub 14 is preferably made of a material harder than the catheter 12 (for example, polypropylene or the like).

The inner needle 16 is a tubular member that has a rigidity that enables puncturing the patient's skin, and is made of, for example, a metal material (such as stainless steel). The inner needle 16 is formed to be longer than the catheter 12. In the initial state of the catheter assembly 10A illustrated in FIG. 1, the needle tip 17 protrudes from the distal opening 12b of the catheter 12 by a predetermined length. In the initial state, the inner needle 16 has an intermediate part in the longitudinal direction being inserted into the catheter hub 14, and a proximal side being held by the needle hub 18.

The needle hub 18 has a hub body 38 arranged in series with the catheter hub 14 in the initial state, and an extending portion 39 extending from the hub body 38 in the distal direction.

In the present embodiment, a pair of extending portions 39 opposing each other along the inner needle 16 on both sides of the inner needle 16 and the catheter hub 14 are provided on both left and right sides of the hub body 38. In the initial state of the catheter assembly 10A, the extending portion 39 extends to the distal side of the proximal end of the catheter hub 14. That is, a distal end of the extending portion 39 is located to be closer to the distal side than the distal end of the catheter hub 14. The extending portion 39 is formed to have an appropriate size (thickness and length) so as to be easily gripped and operated by a user at the time of using the catheter assembly 10A.

Guide protrusions 40 extending along the axial direction of the inner needle 16 are provided on inner surfaces of the pair of extending portions 39 that oppose each other. The left and right guide protrusions 40 are inserted into left and right notches 14b provided in the flange portion 14a of the catheter hub 14, respectively. Accordingly, the catheter hub 14 is stably supported by the needle hub 18 in the initial state, and the rotation of the catheter hub 14 with respect to the needle hub 18 is prevented, so that the hub operation portion 26 can be held to face upward. When the catheter hub 14 is advanced with respect to the needle hub 18, the catheter hub 14 can be smoothly advanced by the guiding action of the guide protrusion 40. Incidentally, the needle hub 18 may have a housing structure with upper and lower sides of the pair of extending portions 39 covered. When the upper sides of the pair of extending portions 39 are covered, a slit through which the hub operation portion 26 can pass is provided in the housing structure.

Next, the deflection suppression mechanism 20 will be described. The deflection suppression mechanism 20 supports the inner needle 16 via the catheter 12 on the distal side of the catheter hub 14 in the initial state of the catheter assembly 10A illustrated in FIG. 1 (the state before the catheter 12 is advanced with respect to the inner needle 16). The deflection suppression mechanism 20 is provided to be movable with respect to the needle hub 18 to be changed from a first state of supporting the inner needle 16 to a second state of releasing the support of the inner needle 16 and allowing the passage of the catheter hub 14.

In the present embodiment, specifically, the deflection suppression mechanism 20 includes: a pair of support arms 42 that can be open and closed; and a restraining portion 44 capable of restraining the pair of support arms 42 in a closed state and releasing the restraint. Hereinafter, in a case where one of the pair of support arms 42 and the other are described to be distinguished from each other, one is described as a "support arm 42a" and the other is described as a "support arm 42b".

The pair of support arms 42 are rotatably connected to the extending portion 39 via a pair of support pins 43. In the illustrated example, the pair of support pins 43 have an axis in the up-down direction, and the pair of support arms 42 supported by the pair of support pins 43 can be open and closed in the left-right direction. In the initial state, a connecting portion between each of the pair of support arms 42 and the extending portion 39 is located to be closer to the distal side than the proximal end of the catheter hub 14.

As illustrated in FIG. 3, each of the support arms 42 is provided with a support groove 53 configured to hold the inner needle 16 in a state where the pair of support arms 42 are closed. In the state where the pair of support arms 42 are closed, the two support grooves 53 form a support hole 54 configured to support the inner needle 16 (the inner needle 16 inserted into the catheter 12). In the initial state of the catheter assembly 10A, the support hole 54 extends along the extending direction of the inner needle 16. The support hole 54 functions as a sliding contact support portion that can support the catheter 12 while sliding against the catheter 12 when the catheter 12 is advanced with respect to the inner needle 16. Hereinafter, the support hole 54 is referred to as a "sliding contact support portion 54". In the initial state of the catheter assembly 10A, a slight gap is formed between an outer surface of the catheter 12 and an inner surface of the sliding contact support portion 54.

In the initial state before the catheter 12 is advanced with respect to the inner needle 16, the sliding contact support portion 54 is located to be closer to the proximal side than the side hole 24 located on the most distal side. In the first embodiment, the sliding contact support portion 54 is provided to be closer to the proximal side than the side hole 24 located on the most proximal side. More specifically, the sliding contact support portion 54 is provided to be slightly closer to the proximal end than the side hole 24 located on the most proximal side. Incidentally, the sliding contact support portion 54 may be provided to be closer to the distal side than some of the plurality of side holes 24 in the initial state of the catheter assembly 10A.

Each of the support arms 42 is provided with engagement grooves 56a and 56b that are bent in a front view in the closed state. Each of the engagement grooves 56a and 56b penetrates through the support arm 42 in the front-rear direction. One engagement groove 56a (hereinafter, referred to as the "first engagement groove 56a") and the other engagement groove 56b (hereinafter, referred to as the "second engagement groove 56b") are bent in mutually opposite directions. Specifically, the first engagement groove 56a is bent downward, and the second engagement groove 56b is bent upward.

As illustrated in FIG. 2, the restraining portion 44 is slidably arranged with respect to the pair of support arms 42. When the restraining portion 44 is pushed by the catheter hub 14 along with the advancement of the catheter hub 14, the restraint on the pair of support arms 42 is released.

The restraining portion 44 has a first restraining protrusion 58a slidably engaging with the first engagement groove 56a, and a second restraining protrusion 58b slidably engaging with the second engagement groove 56b. When the restraining portion 44 is in an initial position (retracted position), the first restraining protrusion 58a and the second restraining protrusion 58b of the restraining portion 44 engage with the first engagement groove 56a and the second engagement groove 56b of the pair of support arms 42, respectively. Thus, the pair of support arms 42 are restrained in the closed state.

The second restraining protrusion 58b is separated from the second engagement groove 56b of the support arm 42 in the distal direction as the restraining portion 44 moves in the distal direction. When the second restraining protrusion 58b is separated from the second engagement groove 56b, the restraint on the pair of support arms 42 by the restraining portion 44 is released, and the pair of support arms 42 can be expanded. Even after the second restraining protrusion 58b is separated from the second engagement groove 56b, the restraining portion 44 is held by the support arm 42a by maintaining the engagement between the first restraining protrusion 58a and the first engagement groove 56a.

A pressed portion 48 is provided at a proximal end of the restraining portion 44. When the catheter hub 14 is advanced with respect to the needle hub 18, the pressed portion 48 is pushed by the distal end of the catheter hub 14, so that the restraining portion 44 is advanced with respect to the pair of support arms 42. A surface of the pressed portion 48 opposing the catheter hub 14 is provided with an inclined portion that is inclined so as to be displaced outward in the left-right direction as proceeding in the proximal direction.

Next, an operation of the catheter assembly 10A will be described.

In use of the catheter assembly 10A, a user (a doctor, a nurse, or the like) grips the needle hub 18 of the catheter assembly 10A in the initial state illustrated in FIG. 1 and punctures a blood vessel of a patient with the catheter 12 and the inner needle 16. At this time, the inner needle 16 is supported by the deflection suppression mechanism 20. Specifically, the inner needle 16 is supported via the catheter 12 by the sliding contact support portion 54 formed between the pair of closed support arms 42, the deflection of the inner needle 16 is suppressed.

After the puncture, a finger is placed on the hub operation portion 26 protruding upward from the catheter hub 14 to push the hub operation portion 26 in the distal direction. Then, the catheter hub 14 and the catheter 12 connected to the hub operation portion 26 move in the distal direction with respect to the needle hub 18, and an insertion length of the catheter 12 into the blood vessel increases.

Figure 4:
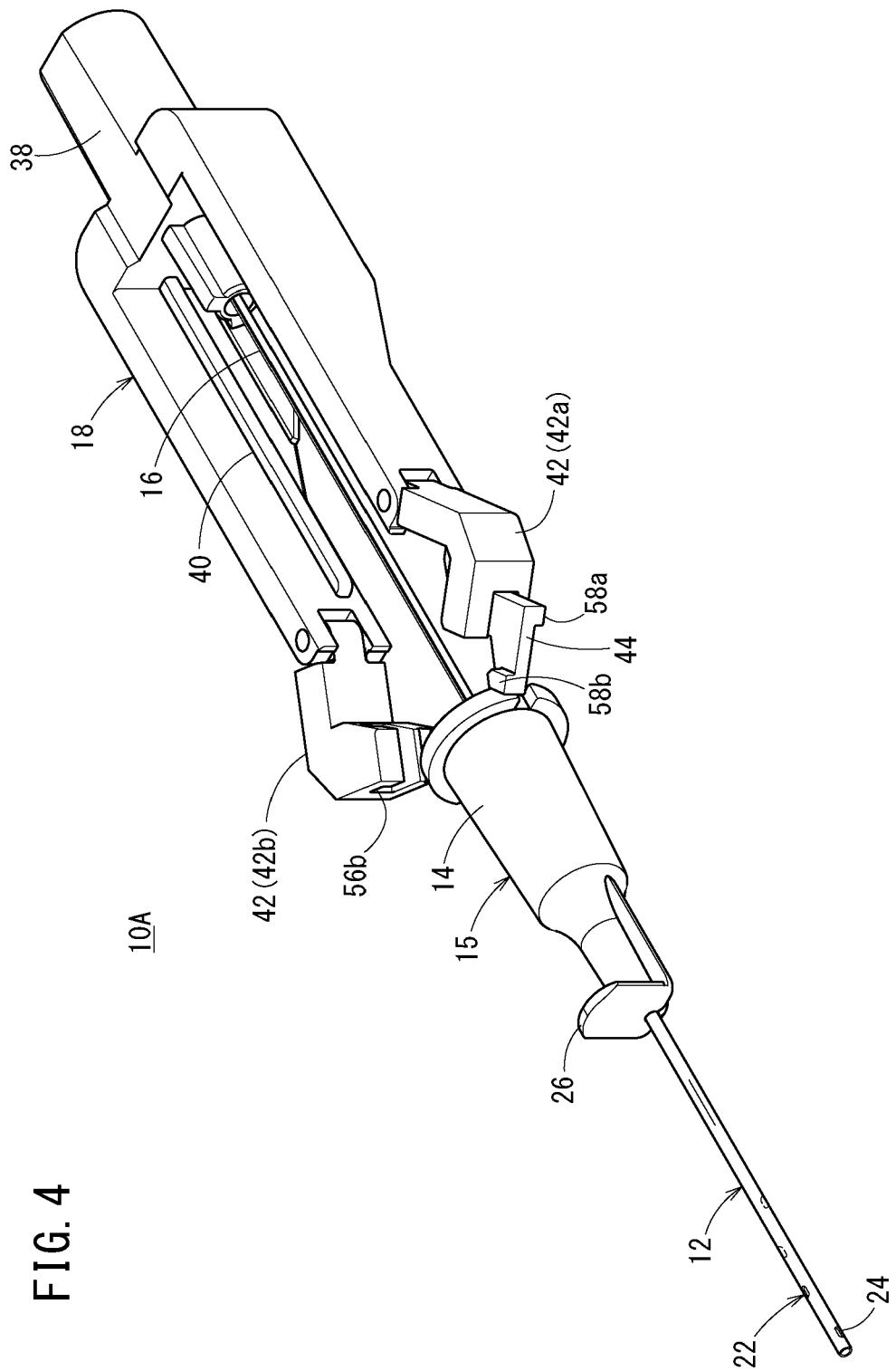
FIG. 4 is a perspective view illustrating a state where a catheter member is advanced in the catheter assembly illustrated in FIG. 1.

The hub operation portion 26 pushes the restraining portion 44 in the distal direction along with the advancement of the catheter hub 14. Accordingly, the restraining portion 44 moves in the distal direction with respect to the pair of support arms 42, and the second restraining protrusion 58b is separated from the second engagement groove 56b. As the second restraining protrusion 58b is separated from the second engagement groove 56b, the restraint on the pair of support arms 42 by the restraining portion 44 is released, and the pair of support arms 42 can be expanded. Further, when the catheter hub 14 is further advanced, the pair of support arms 42 are pushed from the rear side by the hub operation portion 26 and the catheter hub 14 to expand as illustrated in FIG. 4.

After inserting the catheter 12 into the blood vessel by a predetermined length, the needle hub 18 is pulled in the proximal direction in the state of maintaining the position of the catheter member 15. Then, the inner needle 16 moves in the proximal direction in the catheter member 15 so that the inner needle 16 is completely removed from the catheter member 15. As a result, only the catheter member 15 of the catheter assembly 10A remains indwelled on the patient side. After withdrawing the inner needle 16 from the catheter member 15, the catheter hub 14 is fixed to the patient with a dressing material, a tape, or the like.

In this case, the catheter assembly 10A according to the first embodiment has the following effects.

Because the catheter assembly 10A includes the deflection suppression mechanism 20 that supports the inner needle 16 via the catheter 12 to suppress the deflection of the inner needle 16, the deflection of the inner needle 16 at the time of puncture is suppressed. Accordingly, the stable puncture is possible. Because at least one side hole 24 is provided on the circumferential wall of the catheter 12, blood can be suitably suctioned in the case of using the catheter 12 for an infusion or hemodialysis. That is, even when the distal end of the catheter 12 is pasted to a blood vessel wall or the distal end of the catheter 12 is crushed, blood can be suctioned into the catheter 12 through the side hole 24.

Meanwhile, when a syringe is connected to the catheter hub 14 for blood sampling and a pusher of the syringe is pulled, a negative pressure is applied inside the catheter. In the case of the conventional catheter not provided with the side hole 24, the negative pressure inside the catheter increases due to an insufficient blood inflow rate of the catheter, and the catheter is likely to be crushed. In particular, a catheter distal end provided with an opening is easily crushed. On the other hand, because the side hole 24 is provided in the catheter 12 in the catheter assembly 10A, a blood inflow rate into the catheter 12 increases at the time of pulling the pusher of the syringe connected to the catheter hub 14 for blood sampling, and the negative pressure is less likely to be applied to the inside of the catheter 12, and thus, the crushing of the catheter 12 can be prevented. In addition, blood flows into the catheter 12 from the side hole 24, and the negative pressure is less likely to be applied to the inside of the catheter 12 on the distal side of the side hole 24, and thus, the effect of preventing the crushing is great. Even if the distal opening 12b of the catheter 12 is crushed or the distal end of the catheter 12 hits the blood vessel wall, blood can be suctioned from the side hole 24.

Because the sliding contact support portion 54 is located to be closer to the proximal side than the side hole 24 on the most distal side in the initial state of the catheter assembly 10A, it is possible to suppress the damage of the side hole 24 and the variation in sliding resistance at the time of advancing the catheter 12. That is, the side hole 24 of the side flow path structure 22, which is located to be closer to the distal side than the sliding contact support portion 54 in the initial state, does not slide with respect to (slide against) the sliding contact support portion 54 at the time of advancing the catheter 12 with respect to the inner needle 16. Thus, the side hole 24 located to be closer to the distal side than the sliding contact support portion 54 is not damaged by the sliding contact support portion 54 in the initial state, and the side holes 24 does not increase the sliding resistance with respect to the deflection suppression mechanism 20.

In particular, the sliding contact support portion 54 is provided to be closer to the proximal end than the side hole 24 located on the most proximal side in the first embodiment. With this configuration, it is possible to prevent damage of all the side holes 24 and to suppress the variation in sliding resistance with respect to the deflection suppression mechanism 20 at the time of advancing the catheter 12 as much as possible.

Moreover, the sliding contact support portion 54 is provided to be slightly closer to the proximal end than the side hole 24 located on the most proximal side in the first embodiment. With this configuration, the catheter 12 can be effectively supported by the deflection suppression mechanism 20 within a range that does not interfere with the side hole 24.

The catheter 12 has the plurality of side holes 24 arranged at intervals along the longitudinal direction of the catheter 12. With this configuration, the number of the side holes 24 is large, and thus, blood can be reliably suctioned regardless of how the catheter 12 is brought into contact with a blood vessel. Because the number of the side holes 24 is large, the total opening area of the side holes 24 can be increased and the suction resistance can be reduced, and thus, blood can be easily suctioned. Further, the size of each of the side holes 24 can be reduced, and thus, the resistance when the side hole 24 passes through the blood vessel wall decreases, and the operation of inserting the catheter 12 into the blood vessel is easier.

The side hole 24 located on the most proximal side is provided in a lower portion of the catheter 12. With this configuration, when the catheter 12 indwelling in the blood vessel comes out of the blood vessel, the side hole 24 hardly comes out of the blood vessel because the side hole 24 provided on the most proximal side faces downward. That is, when the catheter 12 comes out of the blood vessel, the side hole 24 on the most proximal side that faces downward is caught on the blood vessel wall. At that time, the other side hole 24 is located in the blood vessel.

Second Embodiment

Figure 5:
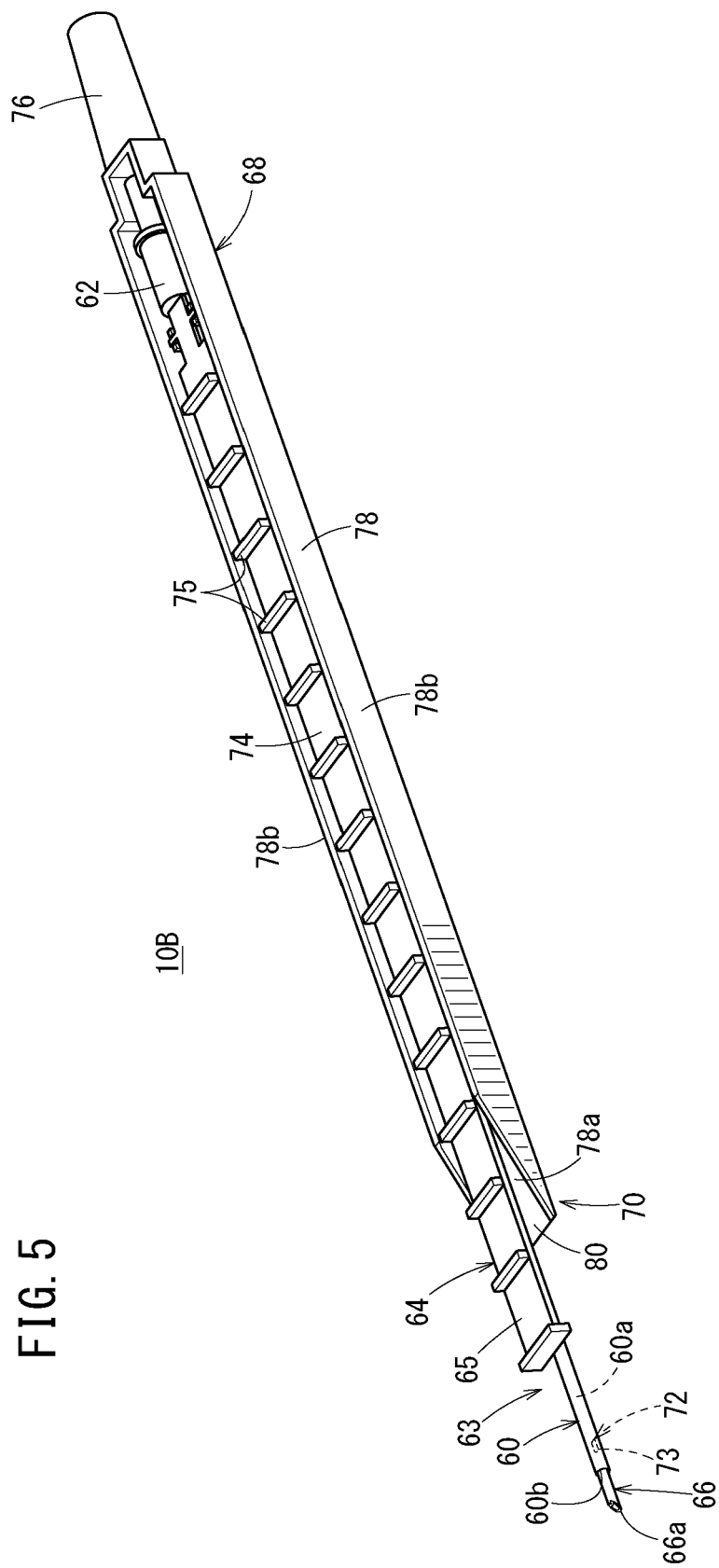
FIG. 5 is a perspective view of a catheter assembly according to a second embodiment of the present invention.

A catheter assembly 10B according to a second embodiment illustrated in FIG. 5 includes: a catheter 60, a catheter hub 62 connected to the catheter 60, a catheter operation member 64 connected to the catheter hub 62; an inner needle 66 inserted into the catheter 60; a needle hub 68 connected to the inner needle 66; and a deflection suppression mechanism 70 that suppresses a deflection of the inner needle 66 at the time of puncture.

The catheter 60 is a small-diameter tubular member that is flexible. The catheter 60 has: a lumen 60a penetrating in the axial direction; a distal opening 60b open at a distal end of the catheter 60; and a proximal opening open at a proximal end of the catheter 60. In an initial state before use (before puncturing a patient), the catheter assembly 10B forms a double-tube structure in which the inner needle 66 is inserted through the catheter 60, and the inner needle 66 protrudes from a distal end of the catheter 60 by a predetermined length.

Figure 6:
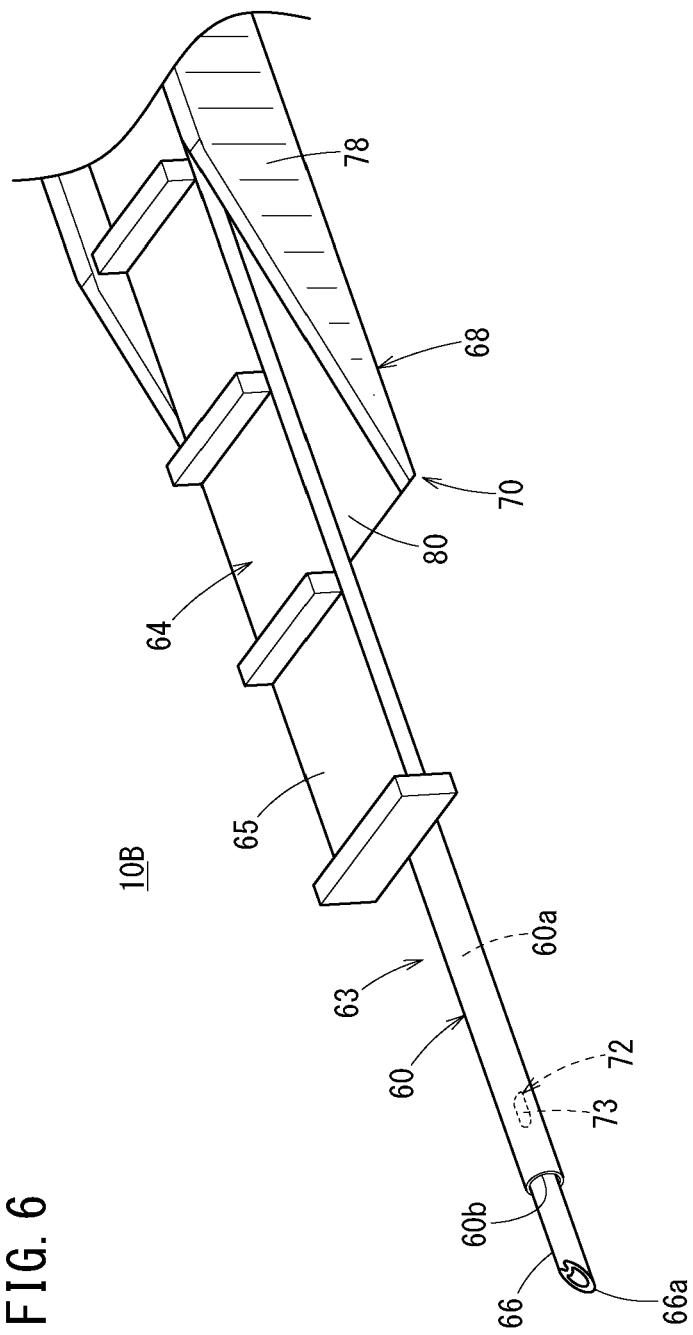
FIG. 6 is an enlarged view of a distal side of the catheter assembly illustrated in FIG. 5.
Figure 7:
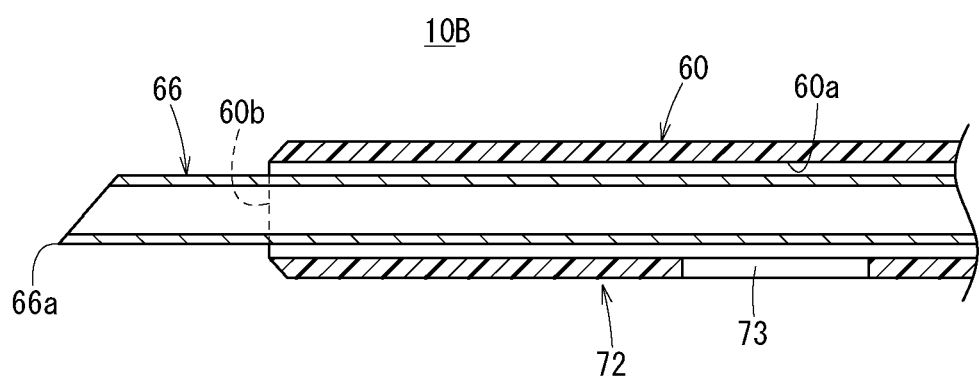
FIG. 7 is a vertical cross-sectional view of the distal side of the catheter assembly illustrated in FIG. 5.

As illustrated in FIGS. 6 and 7, a side flow path structure 72 having only one liquid passage that allows passage of a liquid between an inside and an outside of the catheter 60 is provided between the distal opening 60b and the proximal opening on a circumferential wall of the catheter 60. In the second embodiment, a side hole 73 is provided as the liquid passage. The side hole 73 is provided at a circumferential position corresponding to a circumferential position of a portion of the catheter 60 that contacts a sliding contact support portion 80 to be described later. Specifically, the side hole 73 is provided in a lower portion of the catheter 60. Therefore, the side hole 73 is open downward.

The side hole 73 is formed to be larger than the side hole 24 of the first embodiment illustrated in FIG. 3. A ratio of an opening area of the side hole 73 relative to a cross-sectional area of a catheter lumen is, for example, about 0.5 to 2.0 times, and preferably about 0.7 to 1.0 times. A ratio of a length of the side hole 73 along the axial direction of the catheter 60 relative to an inner diameter of the catheter is, for example, about 0.5 to 3.0 times, and preferably about 0.7 to 2.0 times.

The catheter hub 62 is fixed to the proximal end of the catheter 60. The catheter hub 62 is preferably made of a material harder than the catheter 60. The catheter member 63 is a combination of the catheter 60 and the catheter hub 62.

In FIG. 5, the catheter operation member 64 is connected to the catheter hub 62, and can press a portion between the proximal end and the distal end of the catheter 60 (an intermediate portion in the longitudinal direction of the catheter 60) during a puncturing operation of puncturing a blood vessel with a needle tip 66a of the inner needle 66 and the distal portion of the catheter 60. Specifically, the catheter operation member 64 has a pressing portion 65 that can push the portion between the proximal end and the distal end of the catheter 60. The pressing portion 65 constitutes a part of the deflection suppression mechanism 70.

Further, the catheter operation member 64 includes: an elongated main body 74 arranged along the axial direction (longitudinal direction) of the catheter 60 in a linear state and located on the catheter 60; and a plurality of non-slip ribs 75 provided on an upper surface of the main body 74 at intervals.

The pressing portion 65 is configured by a distal portion of the main body 74. The pressing portion 65 may be configured by a protruding portion of the main body 74 that protrudes downward from the distal portion. The pressing portion 65 is preferably arranged at a position where the deflections of the inner needle 66 and the catheter 60 can be effectively suppressed during the puncturing operation.

The catheter operation member 64 is connected to the catheter hub 62 so as to be rotatable with respect to the catheter hub 62. Specifically, the catheter operation member 64 can be displaced between a first position (a position of the catheter operation member 64 illustrated in FIG. 5) arranged along the longitudinal direction of the catheter 60 and a second position retracted from the catheter 60. When the catheter operation member 64 is located at the first position, the catheter operation member 64 is located on the catheter 60, and the distal portion (pressing portion 65) of the catheter operation member 64 is located between the proximal end and the distal end of the catheter 60. In addition, the separation of the catheter operation member 64 from the catheter hub 62 is prevented when the catheter operation member 64 is located at the first position.

On the other hand, when the catheter operation member 64 is located at the second position, the catheter operation member 64 extends in a direction crossing the longitudinal direction of the catheter 60, and the catheter operation member 64 is separable from the catheter hub 62.

The inner needle 66 has rigidity to be capable of puncturing the skin of the patient. In an initial state of the catheter assembly 10B, the needle tip 66a protrudes from the distal opening 60b of the catheter 60, and a proximal end of the inner needle 66 protrudes toward the proximal side of the proximal portion (catheter hub 62) of the catheter member 63.

The needle hub 68 extends along the longitudinal direction of the inner needle 66 and the catheter 60, and is configured to be long shape as a whole. The needle hub 68 is connected to the inner needle 66 on the proximal side of the inner needle 66, and houses the catheter operation member 64 movably in the longitudinal direction in the initial state. Specifically, the needle hub 68 has a needle holding portion 76 that holds a proximal portion of the inner needle 66, and a housing 78 that extends from the needle holding portion 76 in the distal direction.

When the needle hub 68 is moved in a proximal direction with respect to the catheter 60, the inner needle 66 is also moved in the proximal direction with respect to the catheter 60 along with the movement of the needle hub 68 because the needle hub 68 holds the inner needle 66 at the needle holding portion 76.

The housing 78 has a bottom plate 78a and left and right side walls 78b extending upward from both left and right sides of the bottom plate 78a, and is open at the top and the distal side. The housing 78 functions as a grip that is gripped by a user at the time of using the catheter assembly 10B. A distal portion of the bottom plate 78a is the sliding contact support portion 80 that slides against the catheter 60 at the time of advancing the catheter 60 with respect to the inner needle 66.

The sliding contact support portion 80 constitutes the deflection suppression mechanism 70 together with the pressing portion 65. When the catheter 60 is advanced with respect to the inner needle 66, the catheter 60 (and the inner needle 66) is held between the sliding contact support portion 80 and the pressing portion 65 of the catheter operation member 64. In the initial state before the catheter 60 is advanced with respect to the inner needle 66, the sliding contact support portion 80 is located to be closer to the proximal side than the side hole 73.

The catheter operation member 64 is arranged inside the needle hub 68 (housing 78) configured as described above. The needle hub 68 has a function as a guide member that regulates the moving direction of the catheter operation member 64 when the catheter operation member 64 moves in the distal direction.

Next, an operation of the catheter assembly 10B will be described.

As illustrated in FIG. 5, the inner needle 66 is inserted into the catheter 60, and the needle tip 66a protrudes from the distal end of the catheter 60 by a predetermined length in the initial state of the catheter assembly 10B. During the puncturing operation of puncturing the skin of the patient with the catheter assembly 10B, the user holds the needle hub 68 (housing 78) with one hand (for example, the right hand).

Then, a distal portion of the catheter assembly 10B (the distal portion of the catheter 60 through which the inner needle 66 is inserted) is pressed against a patient while pressing the distal portion of the catheter operation member 64 with an index finger of the one hand, thereby puncturing the skin toward a puncture target blood vessel. The catheter 60 is sandwiched and supported between the pressing portion 65 and the distal portion (sliding contact support portion 80) of the housing 78 in a state where the catheter operation member (pressing portion 65) pushes the intermediate portion of the catheter 60. As a result, the deflections of the inner needle 66 and the catheter 60 are suppressed.

Next, the catheter operation member 64 is advanced by about several mm in the distal direction with the index finger of one hand, whereby the catheter 60 is advanced by about several mm. Next, the catheter operation member 64 is moved in the distal direction with the other hand, whereby the distal end of the catheter 60 is inserted to a target position in the blood vessel. When the catheter 60 is moved in the distal direction with respect to the inner needle 66, the catheter 60 slides with respect to the sliding contact support portion 80.

Next, the needle hub 68 is gripped with one hand while holding the catheter operation member 64 with the other hand, and the needle hub 68 is pulled in the proximal direction. Accordingly, the inner needle 66 is withdrawn from the catheter 60. The catheter operation member 64 may be detached from the catheter hub 62 as needed after removing the inner needle 66 from the catheter 60.

In this case, the catheter assembly 10B according to the second embodiment has the following effects.

Because the catheter assembly 10B includes the deflection suppression mechanism 70 that supports the inner needle 66 via the catheter 60 to suppress the deflection of the inner needle 66, the deflection of the inner needle 66 at the time of puncture is suppressed. Accordingly, the stable puncture is possible. Because the side hole 73 is provided on the circumferential wall of the catheter 60, blood can be suitably suctioned in the case of using the catheter 60 for an infusion or hemodialysis. Because the sliding contact support portion 80 is located to be closer to the proximal side than the side hole 73 in the initial state, damage of the side hole 73 can be suppressed, and a variation in sliding resistance at the time of advancing the catheter 60 can be suppressed.

Only the single side hole 73 is provided at a circumferential position corresponding to a circumferential position of a portion of the catheter 60 that contacts a sliding contact support portion 80. With this configuration, the side hole 73 does not slide with respect to the sliding contact support portion 80 at the time of advancing the catheter 60 even if the large side hole 73 is provided to facilitate the suction, and thus, the side hole 73 is not damaged. In addition, the puncture is easy because there is only one-time resistance when the side hole 73 passes through the blood vessel wall.

Third Embodiment

Figure 8:
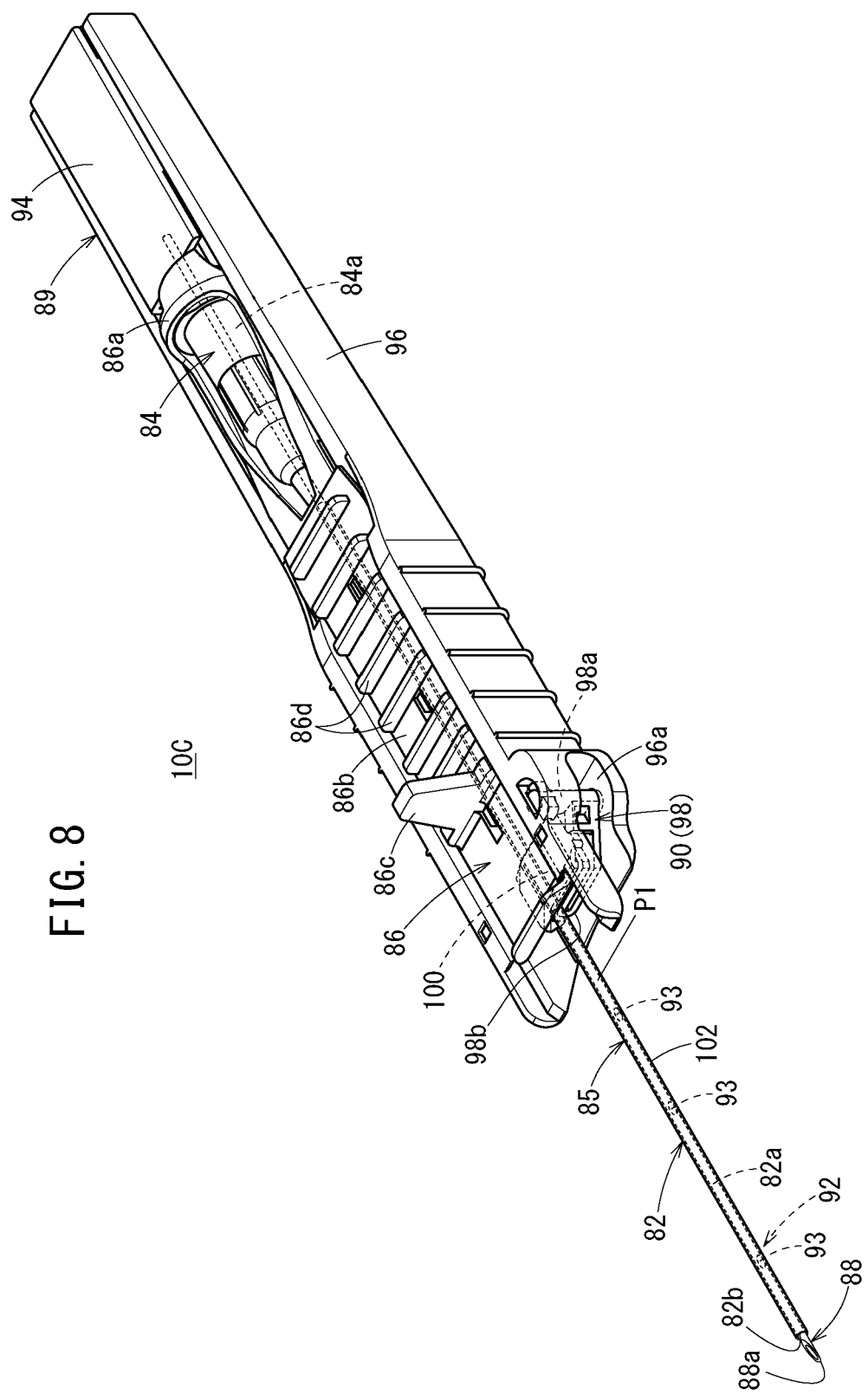
FIG. 8 is a perspective view of a catheter assembly according to a third embodiment of the present invention.

As illustrated in FIG. 8, the catheter assembly 10C includes: a catheter 82; a catheter hub 84 fixedly holding the catheter 82; a catheter operation member 86 mounted to the catheter hub 84; a hollow inner needle 88 removably inserted into the catheter 82; a needle hub 89 fixedly holding the inner needle 88; and a deflection suppression mechanism 90 that suppresses a deflection of the inner needle 88 at the time of puncture. The catheter assembly 10C forms a multi-tube structure (multi-tube portion) in which the catheter 82 and the inner needle 88 are sequentially stacked in an initial state before use illustrated in FIG. 8.

The catheter 82 is a small-diameter tubular member that is flexible and long. The catheter 82 has: a lumen 82a penetrating in the axial direction; a distal opening 82b open at a distal end of the catheter 82; and a proximal opening open at a proximal end of the catheter 82. A distal end of the catheter 82 is reduced in diameter in order to decrease a puncture resistance, and an inner surface of the catheter 82 is in close contact with an outer surface of the inner needle 88 at such a reduced diameter portion in the initial state of the catheter assembly 10C.

Figure 9:
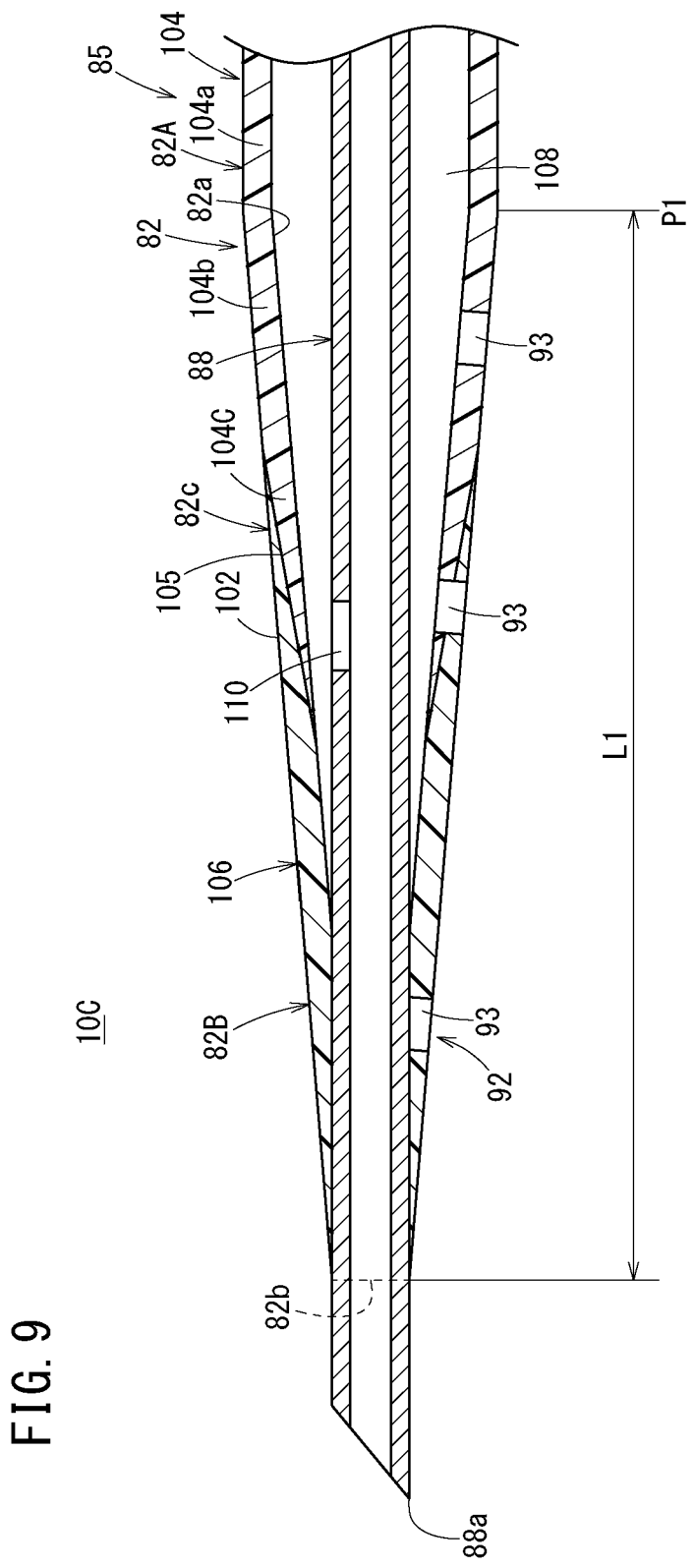
FIG. 9 is a vertical cross-sectional view of the distal side of the catheter assembly illustrated in FIG. 8.

As illustrated in FIG. 9, a flashback flow path 108 for flashback confirmation is formed between an inner circumferential surface of the catheter 82 and an outer circumferential surface of the inner needle 88. The flashback flow path 108 extends from a distal portion to a proximal portion of catheter 82.

A side flow path structure 92, which has at least one liquid passage that allows passage of a liquid between an inside and an outside of the catheter 82, is provided on a circumferential wall of the catheter 82. In the third embodiment, a side hole 93 penetrating from an inner circumferential surface to an outer circumferential surface of the circumferential wall of the catheter 82 is provided as the liquid passage. The side flow path structure 92 has a plurality of the side holes 93 provided at intervals in the longitudinal direction of the catheter 82. All the plurality of side holes 93 is provided in a lower portion of the catheter 82 (open downward). The plurality of side holes 93 may be formed in the same size, or may be formed in different sizes from each other.

The proximal portion of the catheter 82 is fixed to a distal portion of the catheter hub 84 in FIG. 8. The catheter 82 and the catheter hub 84 constitute a catheter member 85. The catheter hub 84 is exposed on the patient's skin in a state where the catheter 82 has been inserted into a blood vessel, and indwells together with the catheter 82 by being pasted with a tape or the like. The catheter hub 84 is formed in a tubular shape tapered in a distal direction.

A hollow portion 84a that communicates with a lumen 82a of the catheter 82 and through which an infusion solution can flow is provided inside the catheter hub 84. A hemostatic valve, a plug, or the like (not illustrated) may be housed inside the hollow portion 84a in order to prevent back-flow of blood at the time of puncture with the inner needle 88 and to allow infusion along with insertion of a connector of an infusion tube.

The inner needle 88 has a rigidity that enables puncture of a skin of a living body, and is arranged to penetrate the lumen 82a of the catheter 82 and the hollow portion 84a of the catheter hub 84. The inner needle 88 is formed to have a total length longer than that of the catheter 82, and a sharp needle tip 88a is provided at a distal end thereof. A lumen penetrating in an axial direction of the inner needle 88 is provided inside the inner needle 88, and this lumen communicates with a distal opening of the inner needle 88. The inner needle 88 may be configured as a solid needle (a needle having no lumen).

The needle hub 89 has a needle holding member 94 fixed to a proximal portion of the inner needle 88, and a housing 96 to which the needle holding member 94 is fixed and that extends along the inner needle 88 and the catheter 82. In the initial state, the catheter assembly 10C houses a part of the multi-tube portion, the catheter hub 84, and the catheter operation member 86 in the housing 96. The needle holding member 94 and the housing 96 may be integrally formed.

When the needle hub 89 is moved in a proximal direction with respect to the catheter 82, the inner needle 88 is also moved in the proximal direction with respect to the catheter 82 along with the movement of the needle hub 89 because the needle hub 89 holds the inner needle 88 at the needle holding member 94.

The catheter operation member 86 is mounted on the catheter hub 84. Thus, when the catheter operation member 86 is advanced relative to the needle hub 89, the catheter member 85 is advanced with respect to the inner needle 88. The catheter operation member 86 has a hub mounting portion 86*a* detachably mounted on the catheter hub 84, and an operation plate portion 86*b* extending from the hub mounting portion 86*a* along the catheter 82 in the distal direction. On an upper surface of the operation plate portion 86*b*, a finger hooking tab 86*c* and a plurality of ribs 86*d* for slip prevention are provided. Incidentally, the catheter operation member 86 is not necessarily provided in the catheter assembly 10C.

The deflection suppression mechanism 90 has a lower support member 98 that supports the lower side of the catheter 82 held by the catheter operation member 86. The lower support member 98 is provided on the distal side of the housing 96. Specifically, the lower support member 98 is rotatably attached to an arrangement concave portion 96*a* provided at a distal portion of the housing 96.

When the skin is punctured with the inner needle 88 and the catheter 82, the lower support member 98 supports the catheter 82 from the lower side, and thus, the deflections of the catheter 82 and the inner needle 88 are suppressed. When the catheter operation member 86 is removed out of the housing 96, the lower support member 98 is rotated toward the outer side of the housing 96 by being pushed by the hub mounting portion 86*a*, and thus, the catheter hub 84 can be separated from the housing 96 in the distal direction.

The lower support member 98 includes: a shaft rod portion 98*a* attached to the distal portion of the housing 96 to be rotatable about an axis in the up-down direction as a center axis; and a support body 98*b* protruding in an orthogonal direction from the axis of the shaft rod 98*a*. The support body 98*b* is formed in a crank shape in a front view, and is elastically deformable in the up-down direction. Accordingly, the lower support member 98 can elastically support the catheter 82. The lower support member 98 has a sliding contact support portion 100 that slides against the catheter 82 when the catheter 82 is advanced with respect to the inner needle 88. In the initial state of the catheter assembly 10C (the state before the catheter 82 is advanced with respect to the inner needle 88), the sliding contact support portion 100 is located to be closer to the proximal side than the side hole 93 provided on the most proximal side. Incidentally, the sliding contact support portion 100 may be provided to be closer to the distal side than some of the plurality of side holes 93 in the initial state of the catheter assembly 10C.

As illustrated in FIG. 9, the catheter 82 has a tapered portion 102 whose outer diameter decreases toward the distal side. The tapered portion 102 constitutes the distal portion of the catheter 82. A length L1 of the tapered portion 102 is set to, for example, about 1 to 60 mm. The plurality of side holes 93 is provided in the tapered portion 102. As illustrated in FIGS. 8 and 9, a proximal position P1 of the tapered portion 102 is located to be slightly closer to the distal side than the sliding contact support portion 100 in the initial state of the catheter assembly 10C.

As illustrated in FIG. 9, the catheter 82 has a catheter body 104 that constitutes a main portion of the catheter 82 and a flexible portion 106 provided at a distal portion of the catheter body 104. Thus, the catheter 82 becomes more flexible toward the most distal portion on the distal side. The flexible portion 106 is exposed from the housing 96 (FIG. 8).

The catheter body 104 accounts for most of the whole length of the catheter 82. Thus, the most distal portion of the catheter body 104 is positioned near the most distal end of the catheter 82. The catheter 82 and the flexible portion 106 are made of a resin material having flexibility. At least the catheter body 104 between the catheter body 104 and the flexible portion 106 has transparency such that a flashback can be confirmed.

The catheter body 104 has: a straight portion 104*a* whose outer diameter is constant along the axial direction; a body tapered portion 104*b* that extends from the straight portion 104*a* in the distal direction and has an outer diameter decreasing in the distal direction; and a distal constituting portion 104*c* that extends from the body tapered portion 104*b* in the distal direction and constitutes a portion up to the most distal portion of the catheter body 104. The body tapered portion 104*b* constitutes a proximal portion of the above-described tapered portion 102.

The catheter 82 is supported by the lower support member (FIG. 8) at a location of the catheter body 104 (the catheter body 104 is supported by the lower support member 98). Accordingly, it is possible to reliably support the catheter 82 and to reduce a sliding resistance at the time of advancing the catheter 82. Moreover, the portion supported by the lower support member 98 (FIG. 8) is located closer to the proximal side than an interface 105 between the catheter body 104 and the flexible portion 106, and thus, it is possible to prevent peeling of the interface 105 caused by sliding of the catheter 82 with respect to the lower support member 98.

Examples of a constituent material of the catheter body 104 include a fluorine-based resin such as polytetrafluoroethylene (PTFE), an ethylene-tetrafluoroethylene copolymer (ETFE), and a perfluoroalkoxy fluorine resin (PFA), an olefin-based resin such as polyethylene and polypropylene or a mixture thereof, polyurethane, polyester, polyamide, a polyether nylon resin, a mixture of the olefin-based resin and an ethylene-vinyl acetate copolymer, and the like. The hardness (Shore A) of the catheter body 104 is, for example, less than 70 D.

The flexible portion 106 includes the most distal portion of the catheter 82. An outer diameter of the flexible portion 106 decreases toward the distal side. The flexible portion 106 constitutes the distal portion of the above-described tapered portion 102. The flexible portion 106 is more flexible than the catheter body 104. That is, an elastic modulus k1 of the catheter body 104 and an elastic modulus k2 of the flexible portion 106 have a relationship of k1>k2. An inner circumferential surface of the flexible portion 106 is in close contact with (fitted to) an outer circumferential surface of the inner needle 88 in a liquid-tight manner over the whole circumference.

Examples of a constituent material of the flexible portion 106 include various rubber materials such as natural rubber, butyl rubber, isoprene rubber, butadiene rubber, styrene-butadiene rubber, silicone rubber, various thermoplastic elastomers such as polyurethanes, polyesters, polyamides, olefins, and styrenes or a mixture thereof, and the like.

In the catheter 82, a single catheter body region 82A where only the catheter body 104 between the catheter body 104 and the flexible portion 106 exists, a single flexible portion region 82B where only the flexible portion 106 between the catheter body 104 and the flexible portion 106 exists, and a mixed region 82C where the catheter body 104 and the flexible portion 106 exist are arranged in the axial direction.

The single catheter body region 82A is a portion of the catheter body 104 present on the proximal side of a most proximal portion of the flexible portion 106. The single flexible portion region 82B is a portion of the flexible portion 106 present on the distal side of the most distal portion of the catheter body 104. The mixed region 82C is a portion in which the catheter body 104 and the flexible portion 106 are stacked in the radial direction. The plurality of side holes 93 is provided in the single catheter body region 82A, the single flexible portion region 82B, and the mixed region 82C. Incidentally, it is sufficient to provide the side holes 93 in any one or more locations of the single catheter body region 82A, the single flexible portion region 82B, and the mixed region 82C.

The hardness of the flexible portion 106 (the single flexible portion region 82B) is, at 23° C., for example, harder than 80 A in JIS hardness (type A) and softer than the catheter body 104, and is preferably 53 D to 64 D in JIS hardness (type D). The flexible portion 106 in the illustrated example is joined to the catheter body 104. Because the axial length and the hardness of the single flexible portion region 82B are set within the above ranges, it is possible to prevent the distal end (the flexible portion 106) of the catheter 82 from being curled at the time of puncture. In addition, it is possible to preferably suppress catching by a blood vessel back wall at the time of inserting the catheter 82. Further, it is possible to suppress crushing of the distal end of the catheter 82 at the time of blood suction.

The interface 105 between the catheter body 104 and the flexible portion 106 is formed in a tapered shape that is inclined at a substantially constant angle with respect to an axis of the catheter 82. In the catheter 82, the interface 105 between the catheter body 104 and the flexible portion 106 is inclined in the distal direction so as to approach the axis (center) of the catheter 82. Thus, the flexible portion 106 is present on the outer side of the catheter body 104 in the mixed region 82C.

Instead of the above configuration having the interface 105, the catheter 82 may be formed so as to become soft in the distal direction by changing each compounding amount of materials different in hardness in the axial direction. In this case, extrusion molding may be performed while changing each extrusion speed of different materials. Alternatively, a content of a plasticizer at the distal portion of the catheter 82 may be increased. In this case, the plasticizer may be applied to the distal portion of the catheter 82.

The inner needle 88 is provided with an introduction path 110 that communicates with the flashback flow path 108 to introduce blood into the flashback flow path 108. The introduction path 110 illustrated in FIG. 9 is a side hole that penetrates through a wall of the inner needle 88 in the radial direction.

Next, functions of the catheter assembly 10C configured as described above will be described.

In use of the catheter assembly 10C, a puncturing operation to puncture the patient's skin with the catheter assembly 10C is performed. In the puncturing operation, the user presses a distal portion of the catheter assembly 10C against the patient while gripping the housing 96 of the catheter assembly 10C in the initial state illustrated in FIG. 8, thereby puncturing the skin toward a puncture target blood vessel. Accordingly, the skin is punctured with each distal portion of the inner needle 88 and the catheter 82.

Next, the user operates the catheter operation member 86 in the distal direction to advance the catheter member 85 (the catheter 82 and the catheter hub 84) while fixing the position of the needle hub 89 (the housing 96). Accordingly, the catheter 82 is inserted to the target position in the blood vessel.

Next, the user pulls the housing 96 in the proximal direction while holding the positions of the catheter operation member 86 and the catheter member 85. Accordingly, the catheter member 85 and the catheter operation member 86 completely come out of the housing 96, and the inner needle 88 is removed from the catheter 82 in the proximal direction.

Next, the catheter operation member 86 is detached from the catheter hub 84. Accordingly, the catheter member 85 is indwelled in the patient. Incidentally, the catheter operation member 86 may be kept attached to the catheter hub 84 depending on a preference of the user.

In this case, the catheter assembly 10C according to the present embodiment has the following effects.

Because the catheter assembly 10C includes the deflection suppression mechanism 90 that supports the inner needle 88 via the catheter 82 to suppress the deflection of the inner needle 88, the deflection of the inner needle 88 at the time of puncture is suppressed. Accordingly, the stable puncture is possible. Because the catheter 82 is provided with the side hole 93, blood can be suitably suctioned in the case of using the catheter 82 for an infusion or hemodialysis. Because the sliding contact support portion 100 is located to be closer to the proximal side than the side hole 93 provided on the most proximal side in the initial state, damage of the side hole 93 can be suppressed, and a variation in sliding resistance at the time of advancing the catheter 82 can be suppressed.

The catheter 82 has the catheter body 104 and the flexible portion 106 provided at the distal portion of the catheter body 104. With this configuration, it is possible to suppress the distal end of the catheter 82 from being caught on a back wall of the blood vessel even when a puncture angle is large. Accordingly, it is possible to prevent the catheter 82 from being hardly inserted into a blood vessel or to prevent a blood vessel wall from being damaged by the distal end of the catheter 82.

The catheter 82 has the tapered portion 102 whose outer diameter decreases toward the distal side, and the lower support member 98 can elastically support the catheter 82. The side hole 93 is provided in the tapered portion 102. In the initial state before the catheter 82 is advanced with respect to the inner needle 88, the sliding contact support portion 100 is located to be closer to the proximal side than the tapered portion 102. In this configuration, the tapered portion 102 contacts the lower support member 98 due to a spring property of the lower support member 98, but a beneficial effect is exhibited because at least the side hole 93 on the most distal side is provided to be closer to the distal side than the sliding contact support portion 100. In particular, because all the side holes 93 are provided to be closer to the distal side than the sliding contact support portion 100 in the third embodiment, it is possible to prevent damage of all side holes 93 and to further effective reduce a variation in sliding resistance with respect to the deflection suppression mechanism 90 at the time of advancing the catheter 82.

Fourth Embodiment

Figure 10:
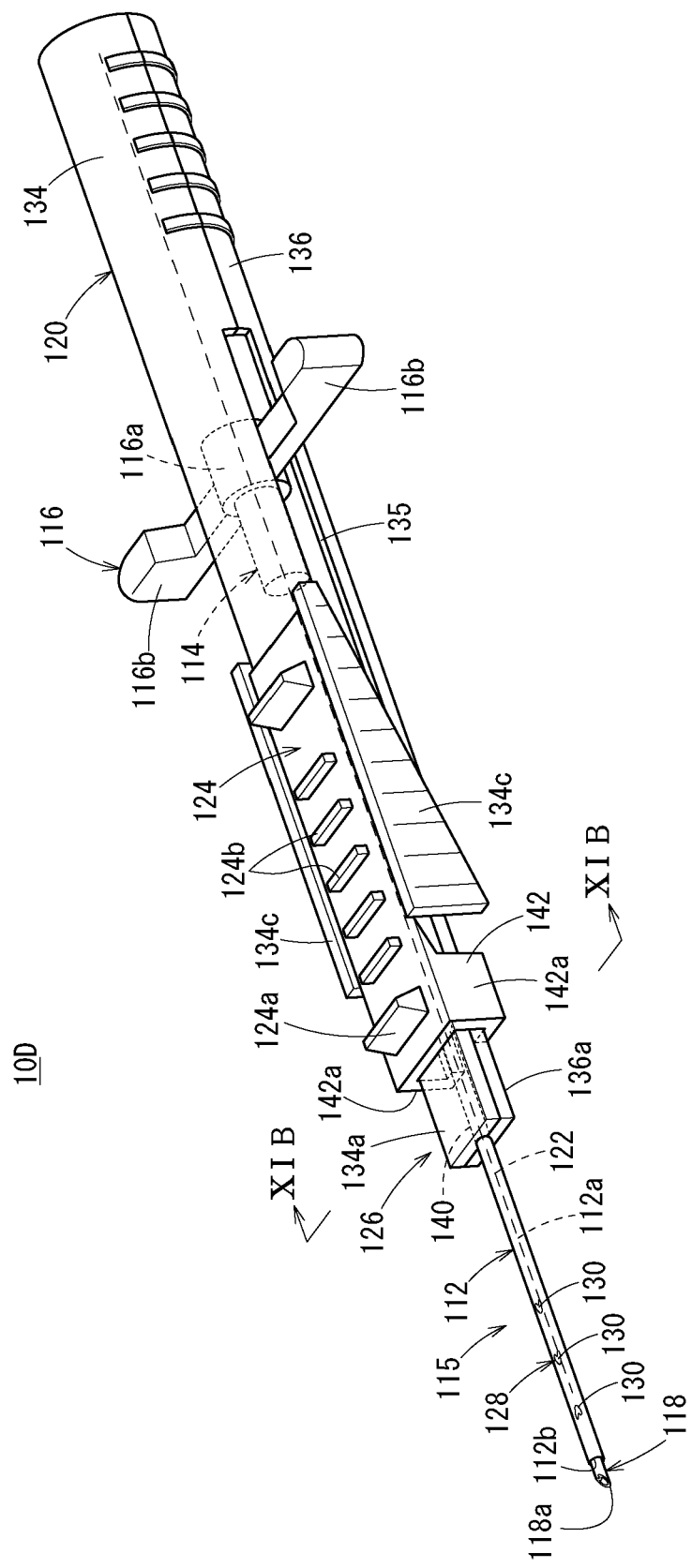
FIG. 10 is a perspective view of a catheter assembly according to a fourth embodiment of the present invention.

A catheter assembly 10D according to a fourth embodiment illustrated in FIG. 10 includes: a catheter 112; a catheter hub 114 connected to the catheter 112; a catheter operation member 116 detachably connected to the catheter hub 114; an inner needle 118 inserted into the catheter 112; a needle hub 120 connected to the inner needle 118; a guide wire 122 inserted through the inner needle 118; a wire operation member 124 connected to the guide wire 122; and a deflection suppression mechanism 126 that suppresses a deflection of the inner needle 118 at the time of puncture.

The catheter 112 has: a lumen 112a penetrating through the catheter 112 in the axial direction; a distal opening 112b open at a distal end of the catheter 112; and a proximal opening open at a proximal end of the catheter 112.

A side flow path structure 128, which has at least one liquid passage that allows passage of a liquid between an inside and an outside of the catheter 112, is provided on a circumferential wall of the catheter 112. In the fourth embodiment, a side hole 130 penetrating from an inner circumferential surface to an outer circumferential surface of the circumferential wall of the catheter 112 is provided as the liquid passage. The side flow path structure 128 has a plurality of the side holes 130 provided at intervals in the longitudinal direction of the catheter 112. The plurality of side holes 130 is all provided in an upper portion of the catheter 112 (open upward). The plurality of side holes 130 may be formed in the same size, or may be formed in different sizes from each other.

Figure 11A:
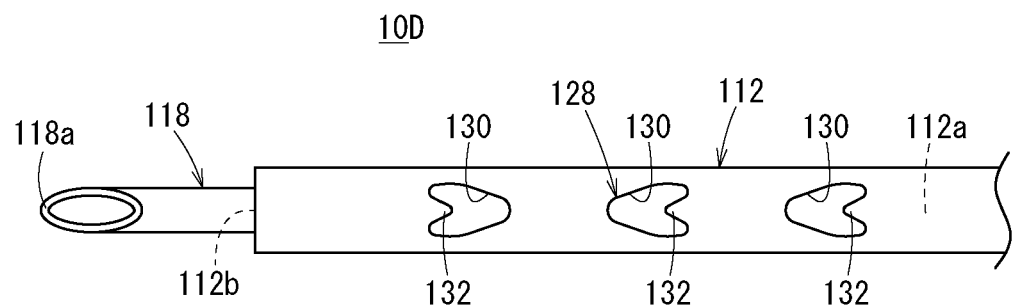
FIG. 11A is a plan view of a distal side of the catheter assembly illustrated in FIG. 10.

As illustrated in FIG. 11A, the side hole 130 has a non-circular shape. Specifically, the side hole 130 is provided with a flap 132 protruding toward the inner side of an opening. The flap 132 is elastically deformable in the radial direction of the catheter 112. The flap 132 protrudes in the distal direction or the proximal direction. In the plurality of side holes 130, all the flaps 132 may protrude in the same direction, or some of the flaps 132 may protrude in a direction different from the other flaps 132 as illustrated in FIG. 11A. The flap 132 may protrude in the circumferential direction of the catheter 112. The flap 132 may protrude in a direction inclined with respect to the axial direction or the circumferential direction of the catheter 112.

The catheter hub 114 is fixed to the proximal portion of the catheter 112. In the initial state of the catheter assembly 10D illustrated in FIG. 10, the catheter hub 114 is housed in the needle hub 120. The catheter operation member 116 has a central base 116a detachably connected to a proximal portion of the catheter hub 114, and a pair of finger hooks 116b extending from the central base 116a to both sides in the left-right direction. In the initial state of the catheter assembly 10D, the central base 116a is housed in the needle hub 120.

The needle hub 120 has an upper housing 134 and a lower housing 136. In the initial state of the catheter assembly 10D, the upper housing 134 and the lower housing 136 vertically overlap, and a distal portion of the needle hub 120 is closed. In addition, distal portions 134a and 136a of the upper housing 134 and the lower housing 136 are held by a pair of restricting arms 142a so as to be embraced, whereby the expansion in the up-down direction is restricted. On the left and right sides of the needle hub 120, slits 135 extending in the longitudinal direction of the needle hub 120 are formed between the upper housing 134 and the lower housing 136. The pair of finger hooks 116b protrude from the slits 135. The upper housing 134 has a pair of side grips 134c inclined to be oblique with respect to the extending direction of the slits 135. In use of the catheter assembly 10D, the user can grip the pair of side grips 134c to puncture a skin of a patient with the inner needle 118 and the catheter 112.

Figure 11B:
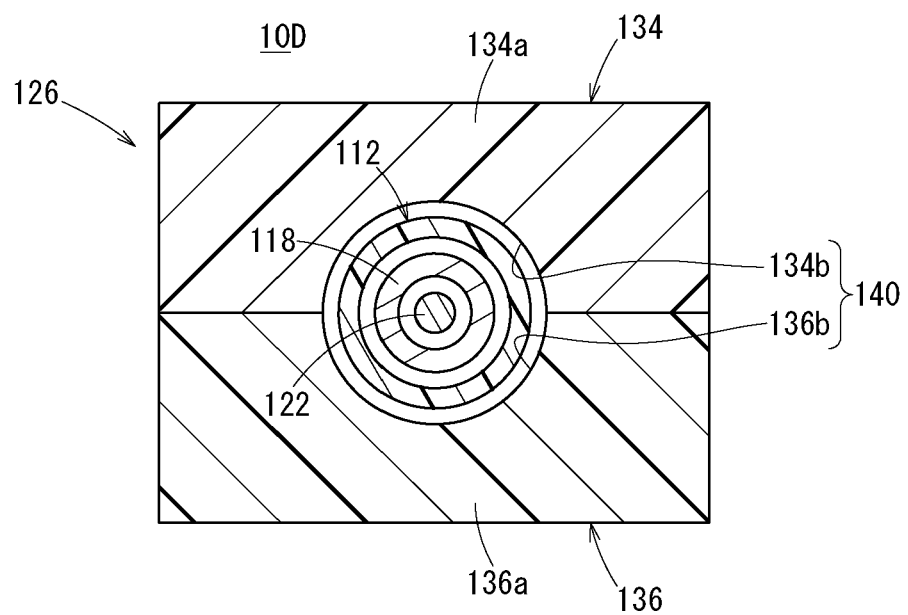
FIG. 11B is a horizontal cross-sectional view along line XIB-XIB in FIG. 10.

The distal portion 134a of the upper housing 134 and the distal portion 136a of the lower housing 136 constitute the deflection suppression mechanism 126. As illustrated in FIG. 11B, a holding groove 134b is formed in the distal portion 134a of the upper housing 134, and a holding groove 136b is formed in the distal portion 136a of the lower housing 136. The two holding grooves 134b and 136b constitute a hole-shaped sliding contact support portion 140 that slides against the catheter 112 when the catheter 112 is advanced with respect to the inner needle 118. In the initial state of the catheter assembly 10D, a slight gap is formed between an outer surface of the catheter 112 and an inner surface of the sliding contact support portion 140.

As illustrated in FIG. 10, the sliding contact support portion 140 is located to be closer to the proximal side than the side hole 130 located on the most distal side in the initial state of the catheter assembly 10D. In the fourth embodiment, the sliding contact support portion 140 is provided to be closer to the proximal side than the side hole 130 located on the most proximal side. Incidentally, the sliding contact support portion 140 may be provided to be closer to the distal side than some of the plurality of side holes 130 in the initial state of the catheter assembly 10D.

The guide wire 122 is a flexible linear member configured to guide the catheter 112 when the catheter 112 is inserted into a blood vessel in order to cause the catheter 112 to indwell in a patient. In the initial state of the catheter assembly 10D, a distal end of the guide wire 122 is located to be closer to the proximal side than a needle tip 118a of the inner needle 118 and is located near the needle tip 118a. The guide wire 122 is slidably inserted into the inner needle 118, and the distal end thereof can protrude from the needle tip 118a.

The wire operation member 124 is an operation portion configured to perform the operation of inserting the guide wire 122 into the blood vessel prior to the operation of inserting the catheter 112 into the blood vessel of the patient. On an upper surface of the wire operation member 124, a finger hooking tab 124a and a plurality of anti-slip ribs 124b are provided.

The wire operation member 124 is connected to a proximal portion of the guide wire 122 via a connecting portion (not illustrated) arranged in the needle hub 120. The wire operation member 124 is provided so as to be displaceable in the front-rear direction with respect to the needle hub 120. The wire operation member 124 has a restricting portion 142 that restricts the distal portion of the needle hub 120 from being open in the up-down direction. The restricting portion 142 has the pair of restricting arms 142a that hold the distal portion of the needle hub 120 in the initial state of the catheter assembly 10D.

Next, functions of the catheter assembly 10D configured as described above will be described.

In use of the catheter assembly 10D, a puncturing operation to puncture the patient's skin with the catheter assembly 10D is performed. In the puncturing operation, the user presses a distal portion of the catheter assembly 10D against the patient while gripping the needle hub 120 of the catheter assembly 10D in the initial state illustrated in FIG. 10, thereby puncturing the skin toward a puncture target blood vessel. Accordingly, the skin is punctured with each distal portion of the inner needle 118 and the catheter 112.

Next, the user operates the wire operation member 124 in the distal direction to cause the guide wire 122 to protrude from the distal end of the inner needle 118. As the guide wire 122 moves in the distal direction, the guide wire 122 is inserted into the blood vessel. When the restricting portion 142 of the wire operation member 124 moves to be closer to the distal side than the distal portion of the needle hub 120 along with the movement of the wire operation member 124 in the distal direction, the restriction on the expansion in the up-down direction by the restricting portion 142 of the distal portion 134a of the upper housing 134 and the distal portion 136a of the lower housing 136 is released.

After the distal end of the guide wire 122 is inserted to the target position in the blood vessel, the user operates the catheter operation member 116 in the distal direction to advance members (the catheter 112 and the catheter hub 114) of the catheter 112 while fixing the position of the needle hub 120. Accordingly, the catheter 112 is inserted to the target position in the blood vessel. At this time, the upper housing 134 is pushed upward by the catheter operation member 116 moving in the distal direction, so that the upper housing 134 is open with respect to the lower housing 136. Accordingly, the movement of the catheter operation member 116 in the distal direction is allowed.

Next, the user pulls the needle hub 120 in the proximal direction while holding the positions of the catheter operation member 116 and the catheter member 115. Accordingly, the catheter member 115 and the catheter operation member 116 completely come out of the needle hub 120, and the inner needle 118 is removed from the catheter 112 in the proximal direction. Next, the catheter operation member 116 is detached from the catheter hub 114. Accordingly, the catheter member 115 is indwelled in the patient.

In this case, the catheter assembly 10D according to the present embodiment has the following effects.

Because the catheter assembly 10D includes the deflection suppression mechanism 126 that supports the inner needle 118 via the catheter 112 to suppress the deflection of the inner needle 118, the deflection of the inner needle 118 at the time of puncture is suppressed. Accordingly, the stable puncture is possible. Because the catheter 112 is provided with the side flow path structure 128 (side hole 130), blood can be suitably suctioned in the case of using the catheter 112 for an infusion or hemodialysis. Because the sliding contact support portion 140 (FIG. 11B) is located to be closer to the proximal side than the side hole 130 provided on the most proximal side in the initial state, damage of the side hole 130 can be suppressed, and a variation in sliding resistance at the time of advancing the catheter 112 can be suppressed.

As illustrated in FIG. 11A, the side flow path structure 128 is provided with the flap 132 protruding toward the inner side of the opening. With this configuration, an opening area is increased by the movement of the flap 132 during blood suction, so that blood can be efficiently suctioned. In addition, the flap 132 does not slide on the sliding contact support portion 140 at the time of advancing the catheter 112, so that damage of the flap 132 can be suppressed.

The side flow path structure 128 (side hole 130) is provided in the upper portion of the catheter 112. With this configuration, blood is easily suctioned because the side hole 130 is in the upper portion even when the distal end of the catheter 112 obliquely indwells.

Fifth Embodiment

A catheter assembly 10E according to a fifth embodiment illustrated in FIG. 12 includes: a catheter 146; a catheter hub 148 connected to the catheter 146; a catheter operation member 151 detachably connected to the catheter hub 148; an inner needle 150 inserted into the catheter 146; a needle hub 152 connected to the inner needle 150; a guide wire 154 inserted through the inner needle 150; a wire operation member 156 connected to the guide wire 154; and a deflection suppression mechanism 158 that suppresses a deflection of the inner needle 150 at the time of puncture.

The catheter 146 has: a lumen 146a penetrating through the catheter 146 in the axial direction; a distal opening 146b open at a distal end of the catheter 146; and a proximal opening open at a proximal end of the catheter 146.

Figure 13A:
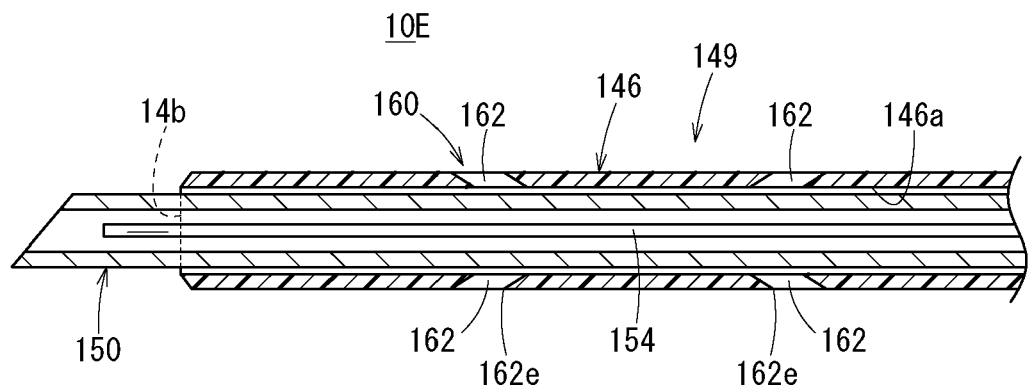
FIG. 13A is a vertical cross-sectional view of a distal side of the catheter assembly illustrated in FIG. 12.

As illustrated in FIG. 13A, a side flow path structure 160, which has at least one liquid passage that allows passage of a liquid between an inside and an outside of the catheter 146, is provided on a circumferential wall of the catheter 146. In the fifth embodiment, a side hole 162 penetrating from an inner circumferential surface to an outer circumferential surface of the circumferential wall of the catheter 146 is provided as the liquid passage. The side flow path structure 160 has a plurality of the side holes 162 provided at intervals in the longitudinal direction of the catheter 146. The side holes 162 extend through the circumferential wall in directions different from each other with respect to an axis of the catheter 146. The side holes 162 extend through the circumferential wall in directions inclined with respect to the axis of the catheter 146. The plurality of side holes 162 includes a side hole 162 inclined toward the distal side and a side hole 162 inclined toward the proximal side. The plurality of side holes 162 may be formed in the same size, or may be formed in different sizes from each other.

The catheter hub 148 is fixed to a proximal portion of the catheter 146 in FIG. 12. The catheter 146 and the catheter hub 148 constitute a catheter member 149. In the initial state of the catheter assembly 10E illustrated in FIG. 12, the catheter hub 148 is housed in the needle hub 152. The catheter operation member 151 has a central base 151a detachably connected to a proximal portion of the catheter hub 148, and a pair of finger hooks 151b extending from the central base 151a to both sides in the left-right direction. The pair of finger hooks 151b is inclined upward toward the outer side in the left-right direction. A plurality of anti-slip protrusions 151c is provided on a lower surface of the finger hook 151b. In the initial state of the catheter assembly 10E, the central base 151a is housed in the needle hub 152.

The needle hub 152 has an upper housing 164 and a lower housing 166. On the left and right sides of the needle hub 152, slits 165 extending in the longitudinal direction of the needle hub 152 are formed between the upper housing 164 and the lower housing 166. The pair of finger hooks 151b protrude from the slits 165. In the initial state of the catheter assembly 10E, the upper housing 164 and the lower housing 166 vertically overlap, and a distal portion of the needle hub 152 is closed. A distal portion 166a of the lower housing 166 is configured to be expandable in the left-right direction. Specifically, the distal portion 166a of the lower housing 166 has a right distal portion 166R and a left distal portion 166L.

The upper housing 164 has a restricting portion 168 that restricts the right distal portion 166R and the left distal portion 166L of the lower housing 166 from being open in the left-right direction. The restricting portion 168 has a pair of restricting arms 168a located on both the left and right sides of the distal portion of the upper housing 164 in the initial state of the catheter assembly 10E. Distal portions of the pair of restricting arms 168a are connected by a distal connecting portion 168b.

Figure 13B:
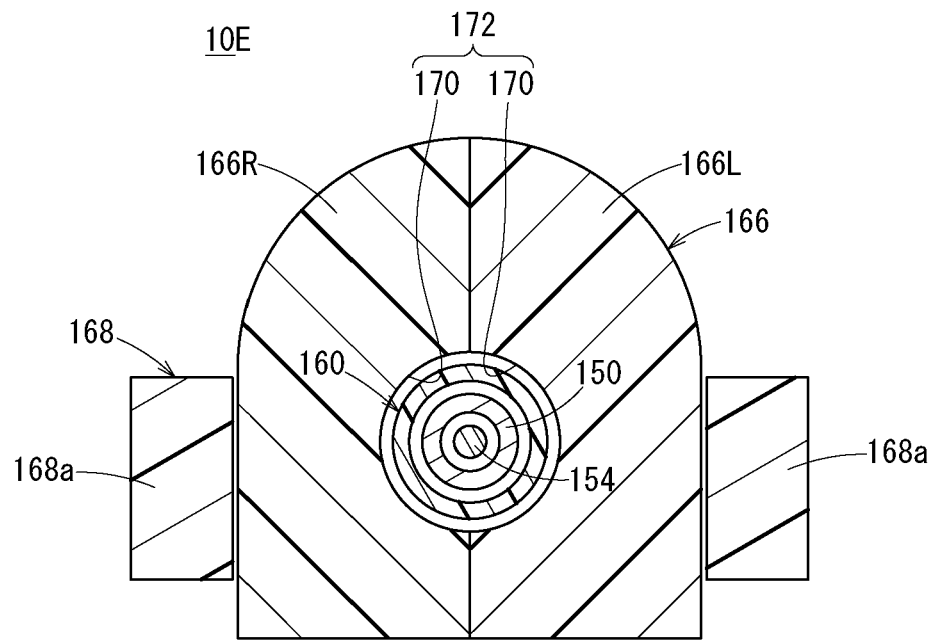
FIG. 13B is a vertical cross-sectional view along line XIIIB-XIIIB in FIG. 12.

The right distal portion 166R and the left distal portion 166L of the lower housing 166 constitute a deflection suppression mechanism 158. As illustrated in FIG. 13B, holding grooves 170 are formed in the right distal portion 166R and the left distal portion 166L, respectively. The two holding grooves 170 constitute a hole-shaped sliding contact support portion 172 that slides against the catheter 146 when the catheter 146 is advanced with respect to the inner needle 150. In the initial state of the catheter assembly 10E, a slight gap is formed between an outer surface of the catheter 146 and an inner surface of the sliding contact support portion 172.

As illustrated in FIG. 12, the sliding contact support portion 172 is located to be closer to the proximal side than the side hole 162 located on the most distal side in the initial state of the catheter assembly 10E. In the fifth embodiment, the sliding contact support portion 172 is provided to be closer to the proximal side than the side hole 162 located on the most proximal side. Incidentally, the sliding contact support portion 172 may be provided to be closer to the distal side than some of the plurality of side holes 162 in the initial state of the catheter assembly 10E.

The wire operation member 156 is an operation portion configured to perform the operation of inserting the guide wire 154 into the blood vessel prior to the operation of inserting the catheter 146 into the blood vessel of the patient. A plurality of finger hooking ribs 156a is provided on an upper surface of the wire operation member 156. The wire operation member 156 is connected to a proximal portion of the guide wire 154 via an intermediate connecting portion (not illustrated) arranged in the needle hub 152. The wire operation member 156 is provided so as to be displaceable in the front-rear direction with respect to the needle hub 152.

Next, functions of the catheter assembly 10E configured as described above will be described.

In use of the catheter assembly 10E, a puncturing operation to puncture the patient's skin with the catheter assembly 10E is performed. In the puncturing operation, the user presses a distal portion of the catheter assembly 10E against the patient while gripping the needle hub 152 of the catheter assembly 10E in the initial state illustrated in FIG. 12, thereby puncturing the skin toward a puncture target blood vessel. Accordingly, the skin is punctured with each distal portion of the inner needle 150 and the catheter 146.

Next, the user operates the wire operation member 156 in the distal direction to cause the guide wire 154 to protrude from the distal end of the inner needle 150. As the guide wire 154 moves in the distal direction, the guide wire 154 is inserted into the blood vessel.

After the distal end of the guide wire 154 is inserted to the target position in the blood vessel, the user operates the catheter operation member 151 in the distal direction to advance the catheter member 149 (the catheter 146 and the catheter hub 148) while fixing the position of the needle hub 152. Accordingly, the catheter 146 is inserted to the target position in the blood vessel. At this time, the upper housing 164 is pushed upward by the catheter operation member 151 moving in the distal direction, so that the upper housing 164 is open with respect to the lower housing 166. As a result, the restriction on expansion of the right distal portion 166R and the left distal portion 166L of the lower housing 166 in the left-right direction by the restricting portion 168 of the upper housing 164 is released. Accordingly, the movement of the catheter operation member 151 in the distal direction is allowed.

Next, the user pulls the needle hub 152 in the proximal direction while holding the positions of the catheter operation member 151 and the catheter member 149. Accordingly, the catheter member 149 and the catheter operation member 151 completely come out of the needle hub 152, and the inner needle 150 is removed from the catheter 146 in the proximal direction.

Next, the catheter operation member 151 is detached from the catheter hub 148. Accordingly, the catheter member 149 is indwelled in the patient. Incidentally, the catheter operation member 151 may be kept attached to the catheter hub 148 depending on a preference of the user.

In this case, the catheter assembly 10E according to the present embodiment has the following effects.

Because the catheter assembly 10E includes the deflection suppression mechanism 158 that supports the inner needle 150 via the catheter 146 to suppress the deflection of the inner needle 150, the deflection of the inner needle 150 at the time of puncture is suppressed. Accordingly, the stable puncture is possible. Because the catheter 146 is provided with the side flow path structure 160 (side hole 162), blood can be suitably suctioned in the case of using the catheter 146 for an infusion or hemodialysis. Because the sliding contact support portion 172 is located to be closer to the proximal side than the side hole 162 provided on the most proximal side in the initial state, damage of the side hole 162 can be suppressed, and a variation in sliding resistance at the time of advancing the catheter 146 can be suppressed.

As illustrated in FIG. 13A, the plurality of side holes 162 is open in directions different from each other with respect to an axis of the catheter 146. With this configuration, a medicinal solution is released in a plurality of directions in the blood vessel at the time of administering the medicinal solution, and reactions cancel each other out, so that the catheter 146 hardly moves in the blood vessel. Therefore, it is possible to prevent the catheter 146 from deviating from an appropriate indwelling position.

The plurality of side holes 162 is open in directions inclined with respect to the axis of the catheter 146. In this configuration, an edge 162e is formed by providing the side hole 162 obliquely, but breakage of the edge 162e is effectively prevented because the side hole 162 does not slide with respect to the sliding contact support portion 172 of the deflection suppression mechanism 158.

Sixth Embodiment

Figure 14:
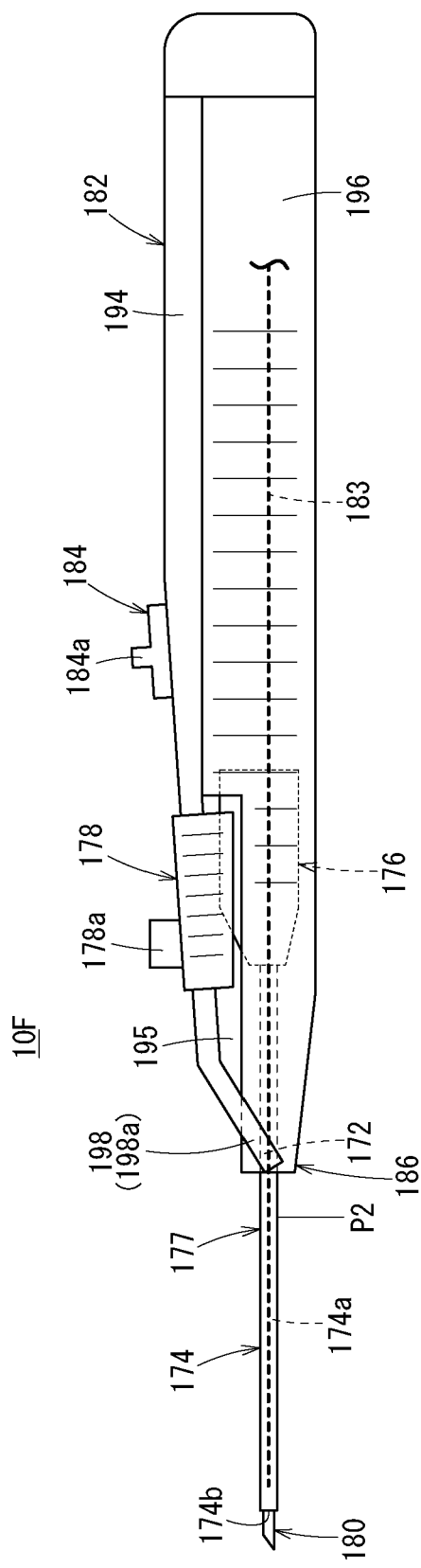
FIG. 14 is a side view of a catheter assembly according to a sixth embodiment of the present invention.

A catheter assembly 10F according to a sixth embodiment illustrated in FIG. 14 includes: a catheter 174; a catheter hub 176 connected to the catheter 174; a catheter operation member 178 detachably connected to the catheter hub 176; an inner needle 180 inserted into the catheter 174; a needle hub 182 connected to the inner needle 180; a guide wire 183 inserted through the inner needle 180; a wire operation member 184 connected to the guide wire 183; and a deflection suppression mechanism 186 that suppresses a deflection of the inner needle 180 at the time of puncture.

The catheter 174 has: a lumen 174a penetrating through the catheter 174 in the axial direction; a distal opening 174b open at a distal end of the catheter 174; and a proximal opening open at a proximal end of the catheter 174.

Figure 15:
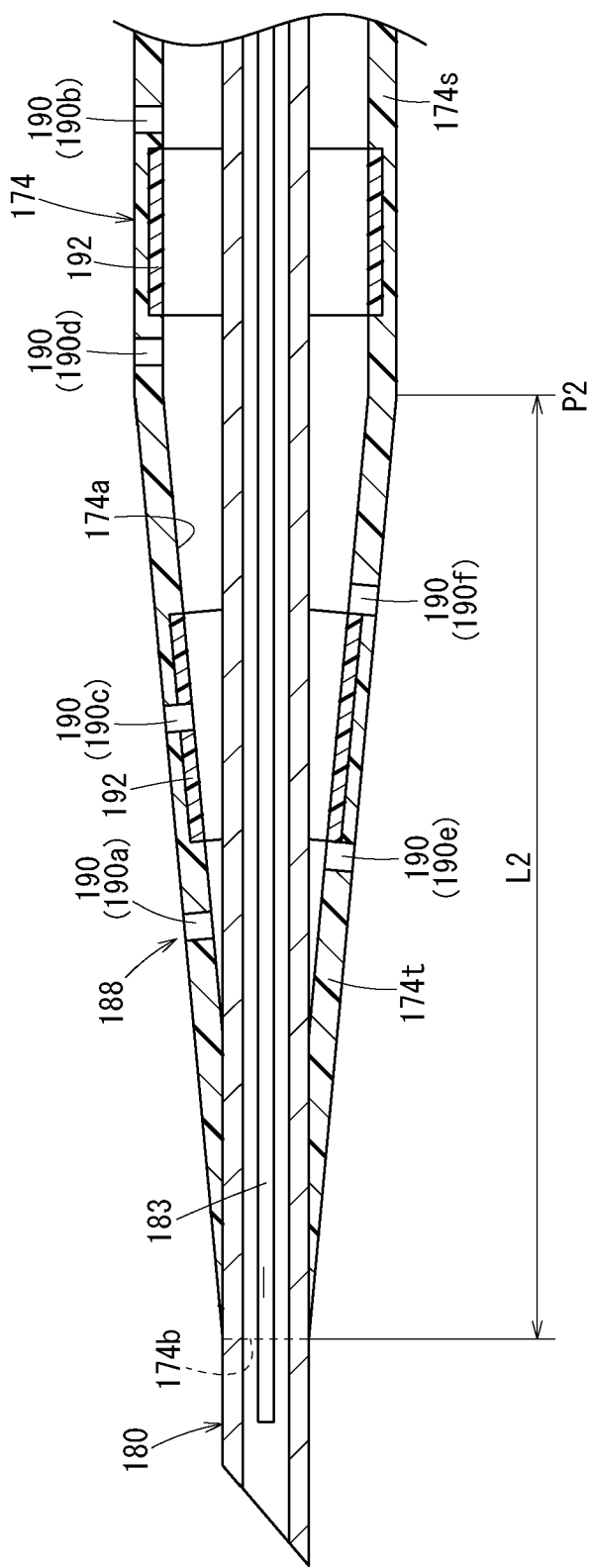
FIG. 15 is a vertical cross-sectional view of a distal side of the catheter assembly illustrated in FIG. 14.

As illustrated in FIG. 15, a side flow path structure 188, which has at least one liquid passage that allows passage of a liquid between an inside and an outside of the catheter 174, is provided on a circumferential wall of the catheter 174. In the sixth embodiment, a side hole 190 penetrating from an inner circumferential surface to an outer circumferential surface of the circumferential wall of the catheter 174 is provided as the liquid passage. The side flow path structure 188 has a plurality of the side holes 190 provided at intervals in the longitudinal direction of the catheter 174. The plurality of side holes 190 may be formed in the same size, or may be formed in different sizes from each other.

A ring 192 made of a material harder than the catheter 174 is embedded in the catheter 174. In the sixth embodiment, a plurality of the rings 192 is arranged at intervals in the longitudinal direction of the catheter 174. At least one side hole 190 is provided at any one or more locations of the distal side of the ring 192, the ring 192 itself, a portion between the ring 192 and the ring 192, the proximal side of the ring 192, a distal boundary of the ring 192, and a proximal boundary of the ring 192.

In FIG. 15, a side hole 190a is provided at the distal side of the ring 192. A side hole 190b is provided at the proximal side of the ring 192. A side hole 190c is provided at the ring 192 itself (penetrates through a wall of the ring 192). A side hole 190d is provided between the ring 192 and the ring 192. A side hole 190e is provided at the distal boundary of the ring 192. A side hole 190f is provided at the proximal boundary of the ring 192.

The catheter 174 has a straight portion 174s whose outer diameter is constant in the axial direction, and a tapered portion 174t that is provided to be closer to the distal side than the straight portion 174s and has an outer diameter decreasing toward the distal side. A length L2 of the tapered portion 174t is set to, for example, about 1 to 60 mm. The ring 192 is provided at any one or more locations of the tapered portion 174t and the straight portion 174s.

The catheter hub 176 is fixed to a proximal portion of the catheter 174 in FIG. 14. The catheter 174 and the catheter hub 176 constitute a catheter member 177. In the initial state of the catheter assembly 10F illustrated in FIG. 14, the catheter hub 176 is housed in the needle hub 182. The catheter operation member 178 is supported by an upper housing 194 of the needle hub 182, which will be described later, so as to be slidable in the front-rear direction. A finger hooking protrusion 178a is provided on an upper surface of the catheter operation member 178.

The needle hub 182 has the upper housing 194 and a lower housing 196. On the left and right sides of the needle hub 182, slits 195 extending in the longitudinal direction of the needle hub 182 are formed between the upper housing 194 and the lower housing 196. The wire operation member 184 is engaged with the catheter hub 176 via the slit 195.

In the initial state of the catheter assembly 10F, the upper housing 194 and the lower housing 196 vertically overlap, and a distal portion of the needle hub 182 is closed. A distal portion of the lower housing 196 is configured to be expandable in the left-right direction. The distal portion of the lower housing 196 has a right distal portion and a left distal portion. The upper housing 194 has a restricting portion 198 that restricts the distal portion of the lower housing 196 from being open in the left-right direction. The restricting portion 198 has a pair of left and right restricting arms 198a located on both the left and right sides of the distal portion of the upper housing 194 in the initial state of the catheter assembly 10F.

The right distal portion and the left distal portion of the lower housing 196 constitute a deflection suppression mechanism 186. Although not illustrated, holding grooves 170 (see FIG. 13B) are formed in the right distal portion and the left distal portion of the lower housing 196, respectively, which is similar to the fifth embodiment. The two holding grooves 170 constitute the hole-shaped sliding contact support portion 172 (see FIG. 13B) that slides against the catheter 174 when the catheter 174 is advanced with respect to the inner needle 180. In the initial state of the catheter assembly 10F, a slight gap is formed between an outer surface of the catheter 174 and an inner surface of the sliding contact support portion 172.

The sliding contact support portion 172 is located to be closer to the proximal side than the side hole 190 located on the most distal side in the initial state of the catheter assembly 10F. In the sixth embodiment, the sliding contact support portion 172 is provided to be closer to the proximal side than the side hole 190 located on the most proximal side. A proximal position P2 of the tapered portion 174t is located to be slightly closer to the distal side than the sliding contact support portion 172 in the initial state of the catheter assembly 10F. Incidentally, the sliding contact support portion 172 may be provided to be closer to the distal side than some of the plurality of side holes 190 in the initial state of the catheter assembly 10F.

The wire operation member 184 is an operation portion configured to perform the operation of inserting the guide wire 183 into the blood vessel prior to the operation of inserting the catheter 174 into the blood vessel of the patient. A finger hooking rib 184a is provided on an upper surface of the wire operation member 184. The wire operation member 184 is connected to the guide wire 183 via an intermediate connecting portion (not illustrated) arranged in the needle hub 182. The wire operation member 184 is provided so as to be displaceable in the front-rear direction with respect to the upper housing 194 of the needle hub 182.

Next, functions of the catheter assembly 10F configured as described above will be described.

In use of the catheter assembly 10F, a puncturing operation to puncture the patient's skin with the catheter assembly 10F is performed. In the puncturing operation, the user presses a distal portion of the catheter assembly 10F against the patient while gripping the needle hub 182 of the catheter assembly 10F in the initial state illustrated in FIG. 14, thereby puncturing the skin toward a puncture target blood vessel. Accordingly, the skin is punctured with each distal portion of the inner needle 180 and the catheter 174.

Next, the user operates the wire operation member 184 in the distal direction to cause the guide wire 183 to protrude from the distal end of the inner needle 180. As the guide wire 183 moves in the distal direction, the guide wire 183 is inserted into the blood vessel.

After the distal end of the guide wire 183 is inserted to the target position in the blood vessel, the user operates the catheter operation member 178 in the distal direction to advance the catheter member 177 (the catheter 174 and the catheter hub 176) while fixing the position of the needle hub 182. Accordingly, the catheter 174 is inserted to the target position in the blood vessel. At this time, the upper housing 194 is pushed upward by the catheter operation member 178 moving in the distal direction, so that the upper housing 194 is open with respect to the lower housing 196. As a result, the restriction on expansion of the right distal portion and the left distal portion of the lower housing 196 in the left-right direction by the restricting portion 198 of the upper housing 194 is released. Accordingly, the movement of the catheter operation member 178 in the distal direction is allowed.

Next, the user pulls the needle hub 182 in the proximal direction while holding the positions of the catheter operation member 178 and the catheter member 177. Accordingly, the catheter member 177 and the catheter operation member 178 completely come out of the needle hub 182, and the inner needle 180 is removed from the catheter 174 in the proximal direction.

Next, the catheter operation member 178 is detached from the catheter hub 176. Accordingly, the catheter member 177 is indwelled in the patient. Incidentally, the catheter operation member 178 may be kept attached to the catheter hub 176 depending on a preference of the user.

In this case, the catheter assembly 10F according to the present embodiment has the following effects.

Because the catheter assembly 10F includes the deflection suppression mechanism 186 that supports the inner needle 180 via the catheter 174 to suppress the deflection of the inner needle 180, the deflection of the inner needle 180 at the time of puncture is suppressed. Accordingly, the stable puncture is possible. Because the catheter 174 is provided with the side flow path structure 188 (side hole 190), blood can be suitably suctioned in the case of using the catheter 174 for an infusion or hemodialysis. Because the sliding contact support portion 172 is located to be closer to the proximal side than the side hole 190 provided on the most proximal side in the initial state, damage of the side hole 190 can be suppressed, and a variation in sliding resistance at the time of advancing the catheter 174 can be suppressed.

A ring 192 made of a material harder than the catheter 174 is embedded in the catheter 174. With this configuration, the catheter 174 is reinforced by the ring 192, and thus, it is possible to prevent the catheter 174 from being crushed in the blood vessel during blood suction.

Seventh Embodiment

Figure 16:
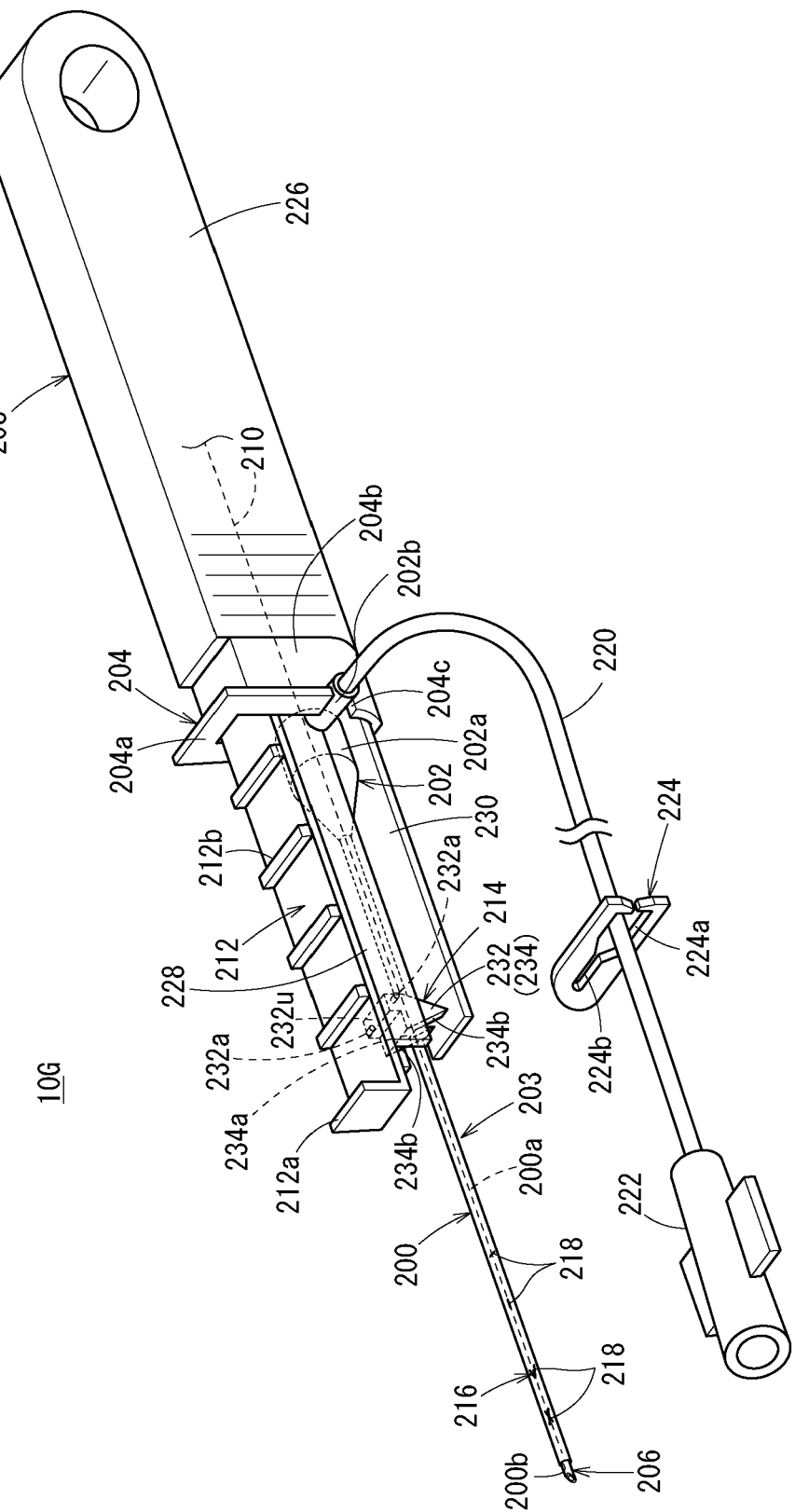
FIG. 16 is a perspective view of a catheter assembly according to a seventh embodiment of the present invention.

A catheter assembly 10G according to a seventh embodiment illustrated in FIG. 16 includes: a catheter 200; a catheter hub 202 connected to the catheter 200; a catheter operation member 204 that moves the catheter hub 202 in the distal direction; an inner needle 206 inserted into the catheter 200; a needle hub 208 connected to the inner needle 206; a guide wire 210 inserted into the inner needle 206; a wire operation member 212 connected to the guide wire 210; and a deflection suppression mechanism 214 that suppresses a deflection of the inner needle 206 at the time of puncture.

Figure 17:
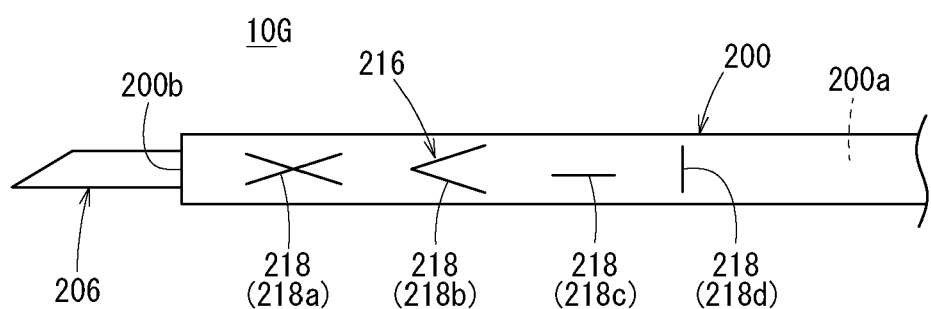
FIG. 17 is a side view of a distal side of the catheter assembly illustrated in FIG. 16.

The catheter 200 has: a lumen 200a penetrating through the catheter 200 in the axial direction; a distal opening 200b open at a distal end of the catheter 200; and a proximal opening open at a proximal end of the catheter 200. As illustrated in FIG. 17, a side flow path structure 216, which has at least one liquid passage that allows passage of a liquid between an inside and an outside of the catheter 200, is provided on a circumferential wall of the catheter 200.

In the seventh embodiment, a slit 218 that is open depending on a pressure in the lumen 200a of the catheter 200 is provided as a liquid passage. An outer end of the slit 218 reaches an outer circumferential surface of the catheter 200, and an inner end of the slit 218 reaches an inner circumferential surface of the catheter 200. When no pressure is applied to the lumen 200a of the catheter 200, the slit 218 is closed. When a positive pressure and a negative pressure are applied to the lumen 200a of the catheter 200, the slit 218 moves in the radial direction of the catheter 200, so that the flow path is opened.

The side flow path structure 216 has a plurality of the slits 218 (218a to 218d) provided at intervals in the longitudinal direction of the catheter 200. The slit 218a is formed in an X shape. The slit 218b is formed in a V shape. The slit 218c is formed to be linear along the longitudinal direction of the catheter 200. The slit 218d is formed along the circumferential direction of the catheter 200. The plurality of slits 218 may be formed in the same size, or may be formed in different sizes from each other. The plurality of slits 218 is provided only at any location of an upper portion and left and right transverse portions of the catheter 200. FIG. 17 illustrates an example in which the plurality of slits 218 is provided only in the left transverse portion of the catheter 200.

The catheter hub 202 is fixed to a proximal portion of the catheter 200 in FIG. 16. The catheter 200 and the catheter hub 202 constitute a catheter member 203. In the initial state of the catheter assembly 10G illustrated in FIG. 16, the catheter hub 202 is housed in the needle hub 208. The catheter hub 202 has: a hub body 202a connected to the catheter 200; and a side port 202b protruding from the hub body 202a in a transverse direction (horizontal direction perpendicular to an axis of the hub body 202a). One end of a soft tube 220 is connected to the side port 202b. A connector 222 is connected to the other end of the tube 220. A clamp 224 capable of opening and closing a flow path in the tube 220 is attached to the tube 220. The clamp 224 is formed in a substantially U shape, and has a wide opening portion 224a and a narrow closing portion 224b. As the clamp 224 slides with respect to the tube 220, the opening and closing of the tube 220 can be switched.

The catheter operation member 204 is an annular member that is supported by a distal portion of a housing 226, which will be described later, of the needle hub 208 to be slidable in the front-rear direction. The catheter operation member 204 is provided with a finger hook 204a protruding in a flange shape. A concave portion 204c open in the distal direction is provided on a side wall 204b of the catheter operation member 204. The side port 202b of the catheter hub 202 protrudes in the transverse direction via the concave portion 204c.

The needle hub 208 has: the housing 226 that functions as a grip to be gripped by the user; and an upper extending portion 228 and a lower extending portion 230 that extend in parallel in the distal direction from the distal portion of the housing 226. In an initial state of the catheter assembly 10G, the catheter 200 and the catheter hub 202 are arranged between the upper extending portion 228 and the lower extending portion 230.

The deflection suppression mechanism 214 is provided at a distal portion of the needle hub 208. Specifically, the deflection suppression mechanism 214 includes a support member 232 supported by the upper extending portion 228 so as to be rotatable about the axis in the left-right direction. The support member 232 has a sliding contact support portion 234 (support body) that slides against the catheter 200 when the catheter 200 is advanced with respect to the inner needle 206. A shaft 232a is provided in an upper portion 232u of the support member 232. The shaft 232a is pivotally supported by the upper extending portion 228. In the initial state of the catheter assembly 10G, a distal portion of the wire operation member 212 is located to be closer to the distal side than the upper portion of the support member 232. Thus, the upward rotation of the support member 232 is restricted by the wire operation member 212.

Figure 18:
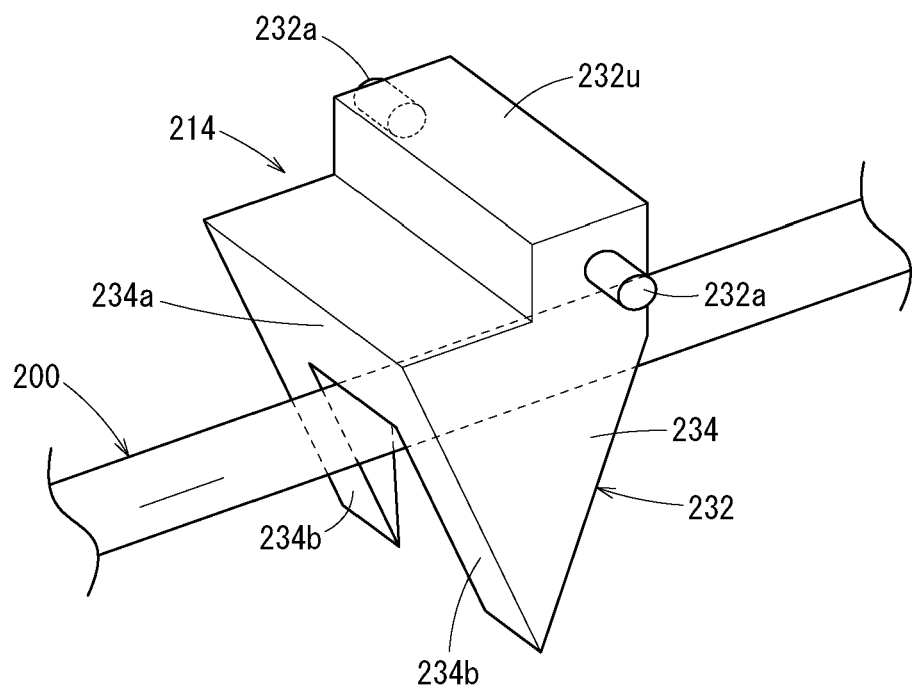
FIG. 18 is a perspective view of a deflection suppression mechanism of the catheter assembly illustrated in FIG. 16.

As illustrated in FIG. 18, the sliding contact support portion 234 has: an upper support portion 234a capable of supporting the catheter 200 from the upper side; and left and right transverse support portions 234b that can support the catheter 200 from the transverse direction. The transverse support portions 234b protrude downward from both left and right ends of the upper support portion 234a. Therefore, the sliding contact support portion 234 is formed in an inverted U shape when viewed from a longitudinal direction of the catheter assembly 10G. In the initial state of the catheter assembly 10G, a slight gap is formed between an outer surface of the catheter 200 and the sliding contact support portion 234.

As illustrated in FIG. 16, the sliding contact support portion 234 is located to be closer to the proximal side than the slit 218 located on the most distal side in the initial state of the catheter assembly 10G. In the seventh embodiment, the sliding contact support portion 234 is provided to be closer to the proximal side than the slit 218 located on the most proximal side. Incidentally, the sliding contact support portion 234 may be provided to be closer to the distal side than some of the plurality of slit 218 in the initial state of the catheter assembly 10G.

The wire operation member 212 is an operation portion configured to perform the operation of inserting the guide wire 210 into the blood vessel prior to the operation of inserting the catheter 200 into the blood vessel of the patient. A finger hooking protrusion 212a and a plurality of anti-slip ribs 212b are provided at a distal end of the wire operation member 212. The wire operation member 212 is supported on an upper surface of the upper extending portion 228 to be slidable in the front-rear direction. One end of the guide wire 210 is arranged near a distal end of the inner needle 206. Although not illustrated in detail, the other end of the guide wire 210 is connected to the wire operation member 212, and an intermediate portion of the guide wire 210 is folded back inside the housing 226.

Next, functions of the catheter assembly 10G configured as described above will be described.

In use of the catheter assembly 10G, a puncturing operation to puncture the patient's skin with the catheter assembly 10G is performed. In the puncturing operation, the user presses a distal portion of the catheter assembly 10G against the patient while gripping the housing 226 of the catheter assembly 10G in the initial state illustrated in FIG. 16, thereby puncturing the skin toward a puncture target blood vessel. Accordingly, the skin is punctured with each distal portion of the inner needle 206 and the catheter 200.

Next, when the user moves the wire operation member 212 in the proximal direction, the guide wire 210 whose intermediate portion has been folded back inside the housing 226 moves in the distal direction inside the inner needle 206. As a result, the guide wire 210 protrudes from the distal end of the inner needle 206 and is inserted into the blood vessel. Along with the movement of the wire operation member 212 in the proximal direction, the distal portion of the wire operation member 212 moves in the proximal direction more than the upper portion of the support member 232. As a result, the restriction on the upward rotation of the support member 232 by the wire operation member 212 is released.

After the distal end of the guide wire 210 is inserted to the target position in the blood vessel, the user operates the catheter operation member 204 in the distal direction to advance the catheter member 203 (the catheter 200 and the catheter hub 202) while fixing the position of the needle hub 208. Accordingly, the catheter 200 is inserted to the target position in the blood vessel. At this time, the support member 232 rotates upward by being pushed by the catheter 200 moving in the distal direction. As a result, the catheter 200 is allowed to be separated from the needle hub 208 in the distal direction.

Next, the user pulls the housing 226 in the proximal direction while holding the positions of the catheter operation member 204 and the catheter member 203. Accordingly, the catheter member 203 and the catheter operation member 204 completely come out of the needle hub 208, and the inner needle 206 is removed from the catheter 200 in the proximal direction. As a result, the catheter 200 is indwelled in the patient's blood vessel.

In this case, the catheter assembly 10G according to the present embodiment has the following effects.

Because the catheter assembly 10G includes the deflection suppression mechanism 214 that supports the inner needle 206 via the catheter 200 to suppress the deflection of the inner needle 206, the deflection of the inner needle 206 at the time of puncture is suppressed. Accordingly, the stable puncture is possible. Because the catheter 200 is provided with the side flow path structure 216 having the liquid passage, blood can be suitably suctioned in the case of using the catheter 200 for an infusion or hemodialysis. Because the sliding contact support portion 234 is located to be closer to the proximal side than the slit 218 provided on the most proximal side in the initial state, damage of the liquid passage can be suppressed, and a variation in sliding resistance at the time of advancing the catheter 200 can be suppressed.

As illustrated in FIG. 17, the liquid passage has the form of the slit 218 that is open depending on the pressure in the lumen 200a of the catheter 200. With this configuration, the slit 218 is closed when no pressure is applied to the lumen 200a of the catheter 200, and thus, the slit 218 is closed at the time of inserting the catheter 200 into a blood vessel. Therefore, it is possible to suppress the resistance when the side flow path structure 216 passes through the blood vessel wall. On the other hand, the slit 218 is open when a positive pressure and a negative pressure are applied to the lumen of the catheter 200, and thus, it is possible to administer a medicinal solution into the blood vessel or to suction the blood without any trouble.

The sliding contact support portion 234 has an upper support portion 234a that can support the catheter 200 from an upper side and a transverse support portion 234b that can support the catheter 200 from the transverse direction (FIG. 18), The slit 218 is provided only at one of the upper portion and the transverse portion of the catheter 200 (FIG. 17). With this configuration, it is possible to effectively suppress damage of the slit 218 and an increase in sliding resistance at the time of advancing the catheter 200.

Figure 19A:
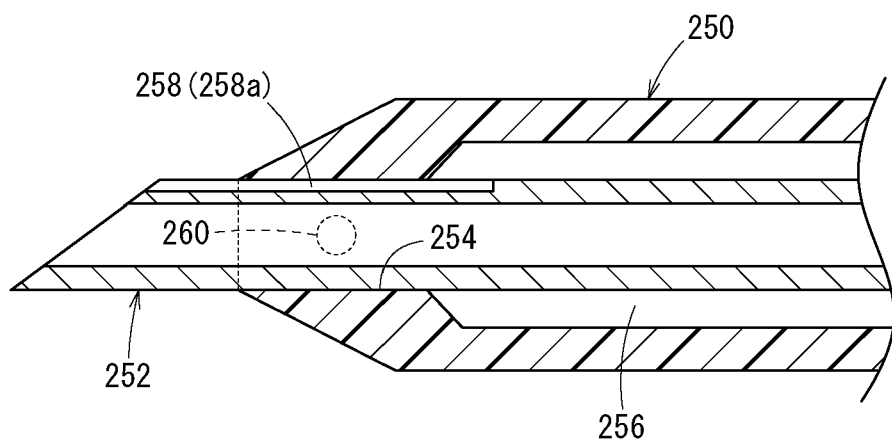
FIG. 19A is a vertical cross-sectional view of an inner needle and a distal side of a catheter according to another aspect.

In any of the above-described embodiments, a catheter 250 and an inner needle 252 illustrated in FIG. 19A may be applied. An inner circumferential surface of a distal portion of the catheter 250 has a close contact portion 254 that is in close contact with an outer circumferential surface of the inner needle 252. A flow path for flashback confirmation (hereinafter, referred to as a "flashback flow path 256") is formed between the catheter 250 and the inner needle 252 on the proximal side of the close contact portion 254. The flashback flow path 256 is formed between the inner circumferential surface of the catheter 250 and the outer circumferential surface of the inner needle 252, and extends up to a proximal opening of the catheter 250. The inner needle 252 is provided with an introduction path 258 that communicates with the flashback flow path 256 to introduce blood into the flashback flow path 256. The introduction path 258 may be a groove 258a extending along the axial direction of the inner needle 252 as in the illustrated example, or may be a hole that penetrates through a circumferential wall of the inner needle 252 in the radial direction.

The close contact portion 254 is provided with a side hole 260 that penetrates through the circumferential wall of the catheter 250 and is open on the inner circumferential surface and an outer circumferential surface of the catheter 250. Therefore, in the initial state, a portion surrounding the side hole 260 in the inner circumferential surface of the distal portion of the catheter 250 is in close contact with the outer circumferential surface of the inner needle 252. The side hole 260 is provided at a position shifted in the circumferential direction from the introduction path 258 (a position not opposing the introduction path 258). The side hole 260 is a liquid passage that allows passage of a liquid between an inside and an outside of the catheter 250. Because the catheter 250 is provided with the side hole 260 as in the above-described embodiments (the catheter assembly 10A and the like), blood can be suitably suctioned in the case of using the catheter 250 for an infusion or hemodialysis.

In particular, in an aspect of FIG. 19A, the side hole 260 is provided in the close contact portion 254, and the side hole 260 is not provided in a portion other than the close contact portion 254. Thus, even in a case where the side hole 260 is outside a blood vessel when a distal end of the inner needle 252 has been inserted into the blood vessel, blood that has flowed into the flashback flow path 256 via the introduction path 258 does not leak out into the body (the inside of the body outside the blood vessel) from the side hole 260 to cause internal bleeding or does not leak out of the body.

Figure 19B:
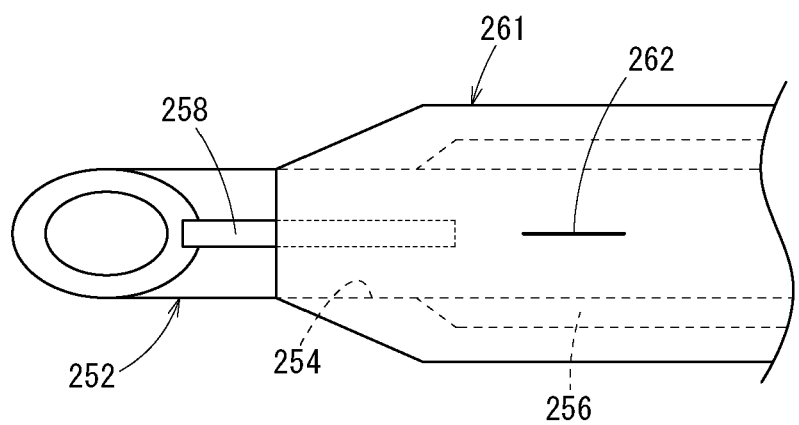
FIG. 19B is a plan view of an inner needle and a distal side of a catheter according to still another aspect.

Although the side hole 260 is provided in the close contact portion 254 in the catheter 250 illustrated in FIG. 19A, a slit 262 that is open depending on a pressure in a lumen of a catheter 261 may be provided on the proximal side of the close contact portion 254 (at a location facing the flashback flow path 256) as in the catheter 261 illustrated in FIG. 19B. Similarly to the above-described slit 218 (see FIG. 17), the slit 262 is a liquid passage that reaches an outer circumferential surface and an inner circumferential surface of the catheter 261 and allows passage of a liquid between an inside and an outside of the catheter 261.

Because the catheter 261 is provided with the slit 262 as in the above-described embodiments, blood can be suitably suctioned in the case of using the catheter 261 for an infusion or hemodialysis. When no pressure is applied to the lumen of the catheter 261 (when the pressure is equal to or less than a predetermined value), the slit 262 is closed. Thus, even in a case where the slit 262 is outside a blood vessel when a distal end of the inner needle 252 has been inserted into the blood vessel, blood that has flowed into the flashback flow path 256 via the introduction path 258 does not leak out into the body (the inside of the body outside the blood vessel) from the slit 262 to cause internal bleeding or does not leak out of the body.

Figure 20:
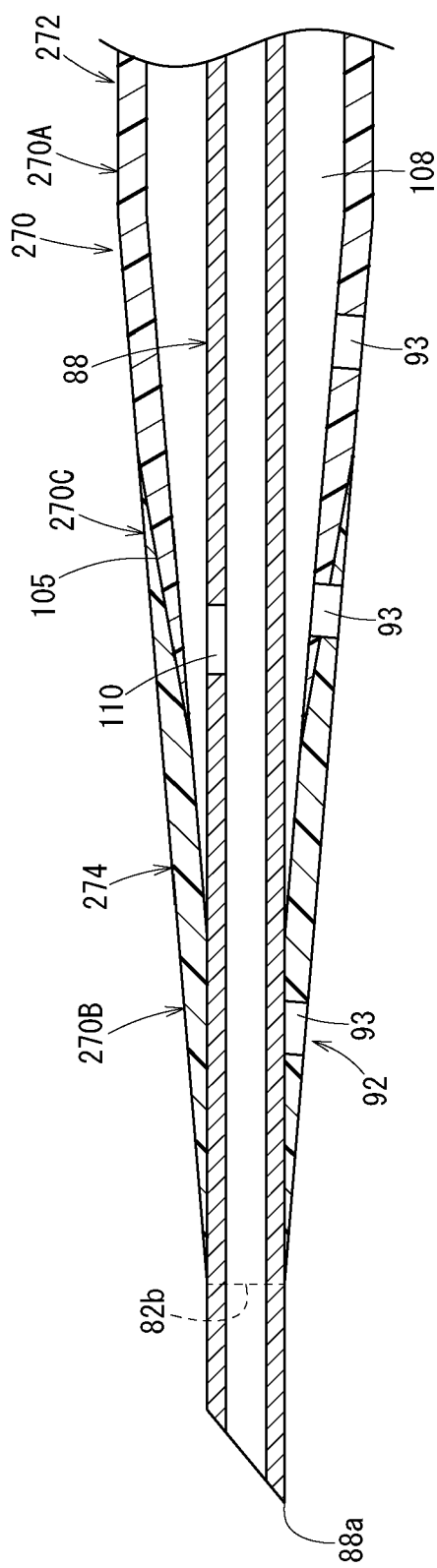
FIG. 20 is a vertical cross-sectional view illustrating another aspect of the catheter assembly illustrated in FIG. 9.

Although the catheter 82 includes the catheter body 104 and the flexible portion 106 provided in the distal portion of the catheter body 104 in the embodiment illustrated in FIG. 9, a catheter 270 having a catheter body 272 and a hard portion 274 provided in a distal portion of the catheter body 272 may be applied as illustrated in FIG. 20. The catheter body 272 is configured to be more flexible than the hard portion 274. Examples of a constituent material of the hard portion 274 include those exemplified as the constituent material of the above-described catheter body 104 (polytetrafluoroethylene or the like).

In the catheter 270, a single catheter body region 270A where only the catheter body 272 between the catheter body 272 and the hard portion 274 exists, a single hard portion region 270B where only the hard portion 274 between the catheter body 272 and the hard portion 274 exists, and a mixed region 270C where the catheter body 272 and the hard portion 274 exist are arranged in the axial direction.

The single catheter body region 270A is a portion of the catheter body 272 present on the proximal side of a most proximal portion of the hard portion 274. The single hard portion region 270B is a portion of the hard portion 274 present on the distal side of a most distal portion of the catheter body 272. The mixed region 270C is a portion in which the catheter body 272 and the hard portion 274 are stacked in the radial direction. The plurality of side holes 93 is provided in the single catheter body region 270A, the single hard portion region 270B, and the mixed region 270C. Incidentally, it is sufficient to provide the side holes 93 in any one or more locations of the single catheter body region 270A, the single hard portion region 270B, and the mixed region 270C.

When the catheter 270 having the hard portion 274 at the distal portion is used, the effect of preventing crushing of the distal portion of the catheter 270 can be enhanced.

Meanwhile, there is a concern regarding a case where the catheter 270 progresses at the same angle as a puncture angle of the inner needle 88 with respect to a blood vessel so that distal end of the catheter 270 hits a back wall of the blood vessel at an acute angle to damage the back wall of the blood vessel. Therefore, it is preferable to use a guide wire at the time of advancing the catheter 270. That is, when the guide wire is advanced into the blood vessel from the inside of the inner needle 88 after puncture of the inner needle 88, the guide wire takes a shape along the blood vessel. Next, when the catheter 270 is advanced along the guide wire, the distal end of the catheter 270 does not hit the back wall of the blood vessel at the acute angle, and thus the back wall of the blood vessel is hardly damaged.

Figure 21A:
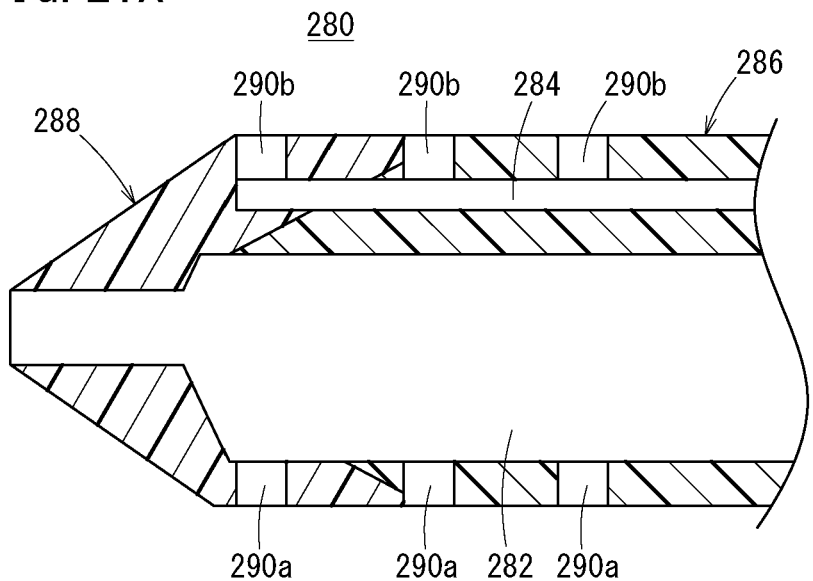
FIG. 21A is a vertical cross-sectional view of a distal side of a multi-lumen type catheter.

In any of the above-described embodiments, a multi-lumen type catheter 280 as illustrated in FIG. 21A may be applied. The catheter 280 has: a main lumen 282 for a first medicinal solution; and a sub-lumen 284 for a second medicinal solution that extends in parallel with the main lumen 282. An inner needle (for example, the inner needle 16 illustrated in FIG. 1) is inserted and arranged in the main lumen 282 in an initial state. The sub-lumen 284 has a smaller flow path cross-sectional area than the main lumen 282. The catheter 280 may be provided with a plurality of the sub-lumens 284. An opening portion that is open in the distal direction may be provided at a distal end of the sub-lumen 284.

The catheter 280 is provided with a catheter body 286 and a distal portion 288 having a different hardness (elastic modulus) from the catheter body 286. The distal portion 288 may be more flexible than the catheter body 286 or harder than the catheter body 286. In another aspect of the catheter 280, the catheter body 286 and the distal portion 288 may have the same hardness.

The catheter 280 is provided with a plurality of side holes 290a communicating with the main lumen 282 and a plurality of side holes 290b communicating with the sub-lumen 284. The number of side holes of either the main lumen 282 or the sub-lumen 284 may be only one. The plurality of side holes 290a and 290b is provided respectively in a region where only the catheter body 286 exists, a region where only the distal portion 288 exists, and a mixed region of the catheter body 286 and the distal portion 288. Incidentally, the side holes 290a and 290b may be provided in any one or more locations of the plurality of regions.

Figure 21B:
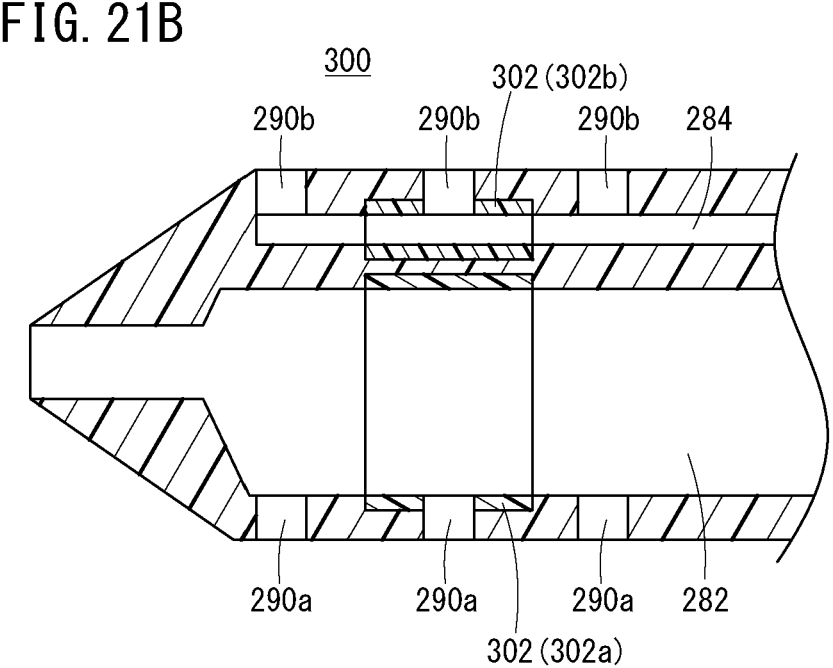
FIG. 21B is a vertical cross-sectional view of a distal side of a multi-lumen type catheter according to another aspect.

As in a multi-lumen type catheter 300 illustrated in FIG. 21B, a reinforcing portion 302 for crushing prevention may be provided in at least one lumen. The reinforcing portion 302 is a ring-shaped or cylindrical member made of a material harder than the catheter 300, and is embedded in the catheter 300. The reinforcing portion 302 has a first reinforcing portion 302a reinforcing the main lumen 282 and a second reinforcing portion 302b reinforcing the sub-lumen 284. The first reinforcing portion 302a surrounds the main lumen 282. The second reinforcing portion 302b surrounds the sub-lumen 284. One of the first reinforcing portion 302a and the second reinforcing portion 302b may be omitted.

At least one side hole 290a communicating with the main lumen 282 may be provided at any position of the distal side of the first reinforcing portion 302a, the proximal side of the first reinforcing portion 302a, an end portion of the first reinforcing portion 302a, and an intermediate portion of the first reinforcing portion 302a. At least one side hole 290b communicating with the sub-lumen 284 may be provided at any position of the distal side of the second reinforcing portion 302b, the proximal side of the second reinforcing portion 302b, an end portion of the second reinforcing portion 302b, and an intermediate portion of the second reinforcing portion 302b.

In any of the above-described embodiments, a reinforcing structure may be added to a catheter (such as the catheter 12 illustrated in FIG. 1) in order to prevent kink or breakage of the catheter. The reinforcing structure is provided, for example, over the entire length of the catheter. Examples of the reinforcing structure include a multilayer tube and a tube with a blade. Alternatively, the reinforcing structure may be provided only in the vicinity of a side hole (such as the side hole 24) (a configuration in FIG. 21B corresponds to this example).

What is claimed is:

1. A catheter assembly comprising:
a catheter comprising a circumferential wall and a distal opening;
an inner needle inserted through the catheter, the inner needle having a sharp needle tip at a distal end of the inner needle; and
a deflection suppression mechanism that supports the inner needle via the catheter to suppress deflection of the inner needle, the deflection suppression mechanism comprising a contact support portion that is configured to support the catheter when the catheter is advanced with respect to the inner needle, wherein:
the circumferential wall of the catheter comprises one or more side holes configured to allow passage of a liquid between an inside and an outside of the catheter, and
in an initial state before the catheter is advanced with respect to the inner needle, the contact support portion is located proximal of a distal-most one of the one or more side holes and a gap is formed between an outer surface of the catheter and an inner surface of the contact support portion.

2. The catheter assembly according to claim 1, wherein:
a first side hole of the one or more side holes comprises a first flap that protrudes from a distal end of the first side hole towards a proximal end of the first side hole.

3. The catheter assembly according to claim 2, wherein:
a second side hole of the one or more side holes comprises a second flap that protrudes from a proximal end of the second side hole towards a distal end of the second side hole.

4. The catheter assembly according to claim 2, wherein:
a second side hole of the one or more side holes comprises a second flap that protrudes from a distal end of the second side hole towards a proximal end of the second side hole.

5. The catheter assembly according to claim 1, wherein:
the one or more side holes include a plurality of side holes, and
a first side hole of the plurality of side holes has a first shape and a second side hole of the plurality of side holes has a second shape that is different from the first shape.

6. The catheter assembly according to claim 1, wherein:
the one or more side holes include a plurality of side holes arranged at intervals along a longitudinal direction of the catheter, and the one or more side holes are located in an upper portion of the catheter.

7. The catheter assembly according to claim 1, wherein:
at least one of the one or more side holes extend through the circumferential wall in a direction inclined with respect to an axis of the catheter.

8. The catheter assembly according to claim 1, wherein:
the circumferential wall comprises a flap that protrudes into at least one of the one or more side holes, and
the flap is elastically deformable in a radial direction of the catheter.

9. The catheter assembly according to claim 1, wherein:
at least one of the one or more side holes has a non-circular shape.

10. The catheter assembly according to claim 1, wherein:
the deflection suppression mechanism further comprises:
an upper housing and a lower housing, and
in the initial state of the catheter, the upper housing and the lower housing vertically overlap.

11. The catheter assembly according to claim 10, further comprising:
a restricting portion comprising restricting arms that support the upper housing and the lower housing such that the restricting arms restrict movement of the upper housing and the lower housing in a direction perpendicular to an axial direction of the catheter.

12. The catheter assembly according to claim 10, wherein:
a distal portion of the upper housing comprises a first groove and a distal portion of the lower housing comprises a second groove, and
the first groove and the second groove form the contact support portion.

13. The catheter assembly according to claim 12, wherein:
the gap comprises a first gap between the first groove and the catheter and a second gap between the second groove and the catheter.

14. The catheter assembly according to claim 1, wherein:
the contact support portion has a cylindrical shape that circumferentially surrounds a portion of the catheter.

15. The catheter assembly according to claim 1, wherein:
in the initial state of the catheter, the contact support portion is located proximal of a proximal-most one of the one or more side holes.

16. The catheter assembly according to claim 1, further comprising:
a catheter hub coupled to a proximal end of the catheter,
a catheter operation member detachably coupled to the catheter hub, and
a pair of finger hooks extending from a central portion of the catheter operation member.

17. The catheter assembly according to claim 16, further comprising:
a needle hub that houses the catheter hub, the needle hub comprising a plurality of slits that extend parallel to an axial direction of the catheter.

18. The catheter assembly according to claim 17, wherein:
a first finger hook of the pair of finger hooks extends through a first slit of the plurality of slits and a second finger hook of the pair of finger hooks extends through a second slit of the plurality of slits.

19. A catheter assembly comprising:
a catheter comprising a circumferential wall and a distal opening;
an inner needle inserted through the catheter, the inner needle having a sharp needle tip at a distal end of the inner needle; and a deflection suppression mechanism that supports the inner needle via the catheter to suppress deflection of the inner needle, the deflection suppression mechanism comprising:
an upper housing and a lower housing,
a restricting portion comprising first and second restricting arms and configured to restrain the upper housing and the lower housing in a direction perpendicular to an axial direction of the catheter, and
a contact support portion that is configured to support the catheter when the catheter is advanced with respect to the inner needle, the contact support portion comprising a support hole formed by support grooves in the upper and lower housing;
the circumferential wall of the catheter comprises one or more side holes configured to allow passage of a liquid between an inside and an outside of the catheter, and
in an initial state before the catheter is advanced with respect to the inner needle, the contact support portion is located proximal of a distal-most one of the one or more side holes and a gap is formed between an outer surface of the catheter and an inner surface of the contact support portion.

20. A catheter assembly comprising:
a catheter comprising a circumferential wall and a distal opening;
an inner needle inserted through the catheter, the inner needle having a sharp needle tip at a distal end of the inner needle;
a catheter operation member comprising a main body; and
a needle hub comprising:
an upper housing, and
a lower housing, wherein:
a distal portion of the upper housing and a distal portion of the lower housing of the needle hub form a deflection suppression mechanism that supports the inner needle via the catheter to suppress deflection of the inner needle,
the deflection suppression mechanism comprises a contact support portion that is configured to support the catheter when the catheter is advanced with respect to the inner needle,
the circumferential wall of the catheter comprises one or more side holes configured to allow passage of a liquid between an inside and an outside of the catheter, and
in an initial state before the catheter is advanced with respect to the inner needle, the contact support portion is located proximal of a distal-most one of the one or more side holes and a gap is formed between an outer surface of the catheter and an inner surface of the contact support portion.

* * * * *